US010821170B2

(12) United States Patent
Yukari et al.

(10) Patent No.: US 10,821,170 B2
(45) Date of Patent: Nov. 3, 2020

(54) DUCK ENTERITIS VIRUS AND THE USES THEREOF

(71) Applicant: CEVA SANTE ANIMALE, Libourne (FR)

(72) Inventors: Saeki Yukari, Ohta-ku (JP); Shuji Saitoh, Yokohama (JP)

(73) Assignee: CEVA SANTE ANIMALE, Libourne (FR)

( * ) Notice: Subject to any disclaimer, the term of this patent is extended or adjusted under 35 U.S.C. 154(b) by 0 days.

(21) Appl. No.: 16/313,174

(22) PCT Filed: Jun. 28, 2017

(86) PCT No.: PCT/EP2017/065987
§ 371 (c)(1),
(2) Date: Dec. 26, 2018

(87) PCT Pub. No.: WO2018/002133
PCT Pub. Date: Jan. 4, 2018

(65) Prior Publication Data
US 2019/0151439 A1    May 23, 2019

(30) Foreign Application Priority Data

Jun. 29, 2016    (EP) .................................... 16176834

(51) Int. Cl.
| A61K 39/145 | (2006.01) |
| A61K 39/12 | (2006.01) |
| C12N 7/00 | (2006.01) |
| A61P 31/16 | (2006.01) |
| A61K 39/39 | (2006.01) |
| C07K 14/465 | (2006.01) |
| C12N 15/52 | (2006.01) |
| A61K 39/00 | (2006.01) |

(52) U.S. Cl.
CPC ............ *A61K 39/145* (2013.01); *A61K 39/12* (2013.01); *A61K 39/39* (2013.01); *A61P 31/16* (2018.01); *C07K 14/465* (2013.01); *C12N 7/00* (2013.01); *C12N 15/52* (2013.01); *A61K 2039/5258* (2013.01); *A61K 2039/54* (2013.01); *A61K 2039/545* (2013.01); *A61K 2039/552* (2013.01); *C12N 2710/16334* (2013.01); *C12N 2710/16343* (2013.01); *C12N 2710/16362* (2013.01); *C12N 2720/10034* (2013.01)

(58) Field of Classification Search
CPC ........ A61K 39/145; A61K 7/00; A61K 39/12; A61K 19/39; A61P 31/36; C12N 7/00
See application file for complete search history.

(56) References Cited

U.S. PATENT DOCUMENTS

| 6,033,670 A | 3/2000 | Bublot et al. |
| 10,202,582 B2 | 2/2019 | Yukari et al. |
| 2018/0187164 A1 | 7/2018 | Yukari et al. |
| 2019/0136208 A1 | 5/2019 | Yukari et al. |
| 2019/0136209 A1 | 5/2019 | Yukari et al. |
| 2019/0144835 A1 | 5/2019 | Yukari et al. |
| 2019/0144836 A1 | 5/2019 | Yukari et al. |

FOREIGN PATENT DOCUMENTS

| CN | 102657861 | 9/2012 |
| FR | 2 757 061 | 6/1998 |
| WO | WO 2014/036735 | 3/2014 |
| WO | WO 2017/001469 | 1/2017 |

OTHER PUBLICATIONS

Aravind, S. et al. "Adaptation and growth kinetics study of an Indian isolate of virulent duck enteritis virus in Vero cells" *Microbial Pathogenesis*, Nov. 13, 2015, pp. 14-19, vol. 78.
Li, H. et al. "Comparative analysis of the genes UL1 through UL7 of the duck enteritis virus and other herpesviruses of the subfamily Alphaherpesvirinae" *Genetics and Molecular Biology*, 2009, pp. 121-128, vol. 32, No. 1.
Li, Y. et al. "Molecular characterization of the genome of duck enteritis virus" *Virology*, Sep. 1, 2009, pp. 151-161, vol. 391, No. 2.
Liu, J. et al. "A Duck Enteritis Virus-Vectored Bivalent Live Vaccine Provides Fast and Complete Protection against H5N1 Avian Influenza Virus Infection in Ducks" *Journal of Virology*, Nov. 2011, pp. 10989-10998, vol. 85, No. 21.
Liu, J. et al. "Recombinant duck enteritis virus works as a single-dose vaccine in broilers providing rapid protection against H5N1 influenza infection" *Antiviral Research*, 2013, pp. 329-333, vol. 97, No. 3.
Liu, X. et al. "Recombinant duck enteritis virus expressing the HA gene from goose H5 subtype avian influenza virus" *Vaccine*, Oct. 15, 2013, pp. 5953-5959, vol. 31, No. 50.
Pan, H.-Q. et al. "Molecular Characterization of the Duck Enteritis Virus UL4 Gene" *Virologica Sinica*, Jun. 2009, pp. 171-178, vol. 24, No. 3.
Wang, J. et al. "Complete genome sequence of virulent duck enteritis virus (DEV) strain 2085 and comparison with genome sequences of virulent and attenuated DEV strains" *Virus Research*, Jul. 5, 2011, pp. 316-325, vol. 160, No. 1.
Wu, Y. et al. "Comparative Genomic Analysis of Duck Enteritis Virus Strains" *Journal of Virology*, Dec. 2012, pp. 13841-13842, vol. 86, No. 24.
Yang, C. et al. "Biological properties of a duck enteritis virus attenuated via serial passaging in chick embryo fibroblasts" *Archives of Virology*, 2015, pp. 267-274, vol. 160, No. 1.
Zou, Z. etal. "Efficient strategy for constructing duck enteritis virus-based live attenuated vaccine against homologous and heterologous H5N1 avian influenza virus and duck enteritis virus infection" *Veterinary Research*, 2015, pp. 1-15, vol. 46, No. 42.

(Continued)

*Primary Examiner* — Bao Q Li
(74) *Attorney, Agent, or Firm* — Saliwanchik, Lloyd & Eisenschenk

(57) ABSTRACT

The present invention relates to DEV and the uses thereof. The invention is particularly suited to vaccinate poultry against avian pathogens.

28 Claims, 9 Drawing Sheets

Specification includes a Sequence Listing.

(56) References Cited

OTHER PUBLICATIONS

Written Opinion in International Application No. PCT/EP2016/065132, dated Sep. 2, 2016, pp. 1-8.
Markham, P. F. et al. "The organisation of the multigene family which encodes the major cell surface protein, pMGA, of *Mycoplasma galilsepticum*" *FEBS Letters*, 1994, pp. 347-352, vol. 352.
Papazisi, L. et al. "The complete genome sequence of the avian pathogen *Mycoplasma gallisepticum* strain $R_{low}$" *Microbiology*, 2003, pp. 2307-2316, vol. 149.
Bijlenga, G. et al. "Development and use of the H strain of avian infectious bronchitis virus from the Netherlands as a vaccine: a review" *Avian Pathology*, Dec. 2004, pp. 550-557, vol. 33, No. 6.
Steel, J. et al. "A combination in-ovo vaccine for avian influenza virus and Newcastle disease virus" *Vaccine*, 2008, pp. 522-531, vol. 26.
Andoh, K. et al. "Turkey herpesvirus with an insertion in the UL3-4 region displays an appropriate balance between growth activity and antibody-eliciting capacity and is suitable for the establishment of a recombinant vaccine" *Archives of Virology*, 2017, pp. 931-941, vol. 162.
Morimoto, T. et al. "Identification of multiple sites suitable for insertion of foreign genes in herpes simplex virus genomes" *Microbiology and Immunology*, 2009, pp. 155-161, vol. 53.
Sun, Y. et al. "Construction of a recombinant duck enteritis virus vaccine expressing hemagglutinin of H9N2 avian influenza virus and evaluation of its efficacy in ducks" *Arch Viral*, 2017, pp. 171-179, vol. 162.
Shen, A.-M. et al. "Transcription phase, protein characteristics of DEV UL45 and prokaryotic expression, antibody preparation of the UL45 des-transmembrane domain" *Virology Journal*, 2010, pp. 1-14, vol. 7, No. 232.
Liu, S. et al. "Molecular characterization of the herpes simplex virus 1 (HSV-1) homologues, UL25 to UL30, in duck enteritis virus (DEV)" *Gene*, 2007, pp. 88-96, vol. 401.
Chen, P. et al. "The vaccine efficacy of recombinant duck enteritis virus expressing secreted E with or without PrM proteins of duck tembusu virus" *Vaccine*, 2014, pp. 5271-5277, vol. 32.
Balan, P. et al. "An analysis of the in vitro and in vivo phenotypes of mutants of herpes simplex virus type 1 lacking glycoproteins gG, gE, gI or the putative gJ" *Journal of General Virology*, 1994, pp. 1245-1258, vol. 75.
Liu, X. et al. "Different linkages in the long and short regions of the genomes of duck enteritis virus Clone-03 and VAC Strains" *Virology Journal*, 2011, pp. 1-12, vol. 8, No. 1.
Wang, J, et al. "Complete genome sequence of virulent duck enteritis virus (DEV) strain 2085 and comparison with genome sequences of virulent and attenuated DEV strains" *Virus Research*, 2011, pp. 316-325, vol. 160.
Wang, J. et al. "Construction of a recombinant duck enteritis virus (DEV) expressing hemagglutinin of H5N1 avian influenza virus based on an infectious clone of DEV vaccine strain and evaluation of its efficacy in ducks and chickens" *Virology Journal*, 2015, pp. 1-14, vol. 12, No. 1.
Weber, P. C. et al. "Rapid Identification of Nonessential Genes of Herpes Simplex Virus Type 1 by Tn5 Mutagenesis" *Science*, May 1, 1987, pp. 576-579, vol. 236.
Written Opinion in International Application No. PCT/EP2017/065987, dated Sep. 1, 2017, pp. 1-5.

| DEV/US4US5del | DEV/US4US5del | DEV/US4US5del | DEV/US4US5del |
| /UL23/Coa5VP2 | /UL26/Coa5VP2 | /UL45/Coa5VP2 | /UL50/Coa5VP2 |

SEQUENCE LISTING

<160> NUMBER OF SEQ IDS NOS: 43

<210> SEQ ID NO 1
<211> LENGTH: 30
<212> TYPE: DNA
<213> ORGANISM: Artificial

```
<220> FEATURE:
<223> OTHER INFORMATION: primer

<400> SEQUENCE: 1
ggcctggtga tgatggcggg atcgttgtat                                        30

<210> SEQ ID NO 2
<211> LENGTH: 30
<212> TYPE: DNA
<213> ORGANISM: Artificial
<220> FEATURE:
<223> OTHER INFORMATION: primer

<400> SEQUENCE: 2
ccatggtgct gcgctcagaa gaactcgtca                                        30

<210> SEQ ID NO 3
<211> LENGTH: 1319
<212> TYPE: DNA
<213> ORGANISM: Artificial
<220> FEATURE:
<223> OTHER INFORMATION: rpsLneo

<400> SEQUENCE: 3
ggcctggtga tgatggcggg atcgttgtat atttcttgac accttttcgg catcgcccta        60
aaattcggcg tcctcatatt gtgtgaggac gttttattac gtgttacga agcaaaagct       120 aaaaccagga gctatttaat ggcaacagtt aaccagctgg tacgcaaacc acgtgctcgc       180
aaagttgcga aaagcaacgt gcctgcgctg gaagcatgcc cgcaaaaacg tggcgtatgt       240
actcgtgtat atactaccac tcctaaaaaa ccgaactccg cgctgcgtaa agtatgccgt       300
gttcgtctga ctaacggttt cgaagtgact tcctacatcg gtggtgaagg tcacaacctg       360
caggagcact ccgtgatcct gatccgtggc ggtcgtgtta aagacctccc gggtgttcgt       420
taccacaccg tacgtggtgc gcttgactgc tccggcgtta agaccgtaa gcaggctcgt       480 tccaagtatg gcgtgaagcg tcctaaggct taaggaggac aatcatgatt gaacaagatg       540
gattgcacgc aggttctccg gccgcttggg tggagaggct attcggctat gactgggcac       600
aacagacaat cggctgctct gatgccgccg tgttccggct gtcagcgcag gggcgcccgg       660 ttcttttgt caagaccgac ctgtccggtg ccctgaatga actgcaggac gaggcagcgc       720
ggctatcgtg gctggccacg acgggcgttc cttgcgcagc tgtgctcgac gttgtcactg       780
aagcgggaag gactggctg ctattggccg aagtgccggg gcaggatctc ctgtcatctc        840
accttgctcc tgccgagaaa gtatccatca tggctgatgc aatgcggcgg ctgcatacgc       900
ttgatccggc tacctgccca ttcgaccacc aagcgaaaca tcgcatcgag cgagcacgta       960
ctcggatgga agccggtctt gtcgatcagg atgatctgga cgaagagcat caggggctcg      1020
cgccagccga actgttcgcc aggctcaagg cgcgcatgcc cgacggcgag gatctcgtcg      1080
tgacccatgg cgatgcctgc ttgccgaata tcatggtgga aaatggccgc ttttctggat      1140
tcatcgactg tggccggctg ggtgtggcgg accgctatca ggacatagcg ttggctaccc      1200
gtgatattgc tgaagagctt ggcggcgaat gggctgaccg cttcctcgtg ctttacggta      1260
tcgccgctcc cgattcgcag cgcatcgcct tctatcgcct tcttgacgag ttcttctga       1319

<210> SEQ ID NO 4
<211> LENGTH: 30
<212> TYPE: DNA
<213> ORGANISM: Artificial
<220> FEATURE:
```

<223> OTHER INFORMATION: primer

<400> SEQUENCE: 4
acgagttctt ctgagcgcag caccatggcc                                30

<210> SEQ ID NO 5
<211> LENGTH: 30
<212> TYPE: DNA
<213> ORGANISM: Artificial
<220> FEATURE:
<223> OTHER INFORMATION: primer

<400> SEQUENCE: 5
tcggaggagg ccatccttaa gagctgtaat                                30

<210> SEQ ID NO 6
<211> LENGTH: 30
<212> TYPE: DNA
<213> ORGANISM: Artificial
<220> FEATURE:
<223> OTHER INFORMATION: primer

<400> SEQUENCE: 6
tacagctctt aaggatggcc tcctccgaga                                30

<210> SEQ ID NO 7
<211> LENGTH: 30
<212> TYPE: DNA
<213> ORGANISM: Artificial
<220> FEATURE:
<223> OTHER INFORMATION: primer

<400> SEQUENCE: 7
gcagtgaaaa aaatgcttta tttgtgaaat                                30

<210> SEQ ID NO 8
<211> LENGTH: 70
<212> TYPE: DNA
<213> ORGANISM: Artificial
<220> FEATURE:
<223> OTHER INFORMATION: primer

<400> SEQUENCE: 8
atggcaacaa tgatagctgt ggtgttagtt tttttgggac gcgttttagg ggcctggtga      60
tgatggcggg                                                            70

<210> SEQ ID NO 9
<211> LENGTH: 70
<212> TYPE: DNA
<213> ORGANISM: Artificial
<220> FEATURE:
<223> OTHER INFORMATION: primer

<400> SEQUENCE: 9
ttaaactaat ggaacgcgtt ggaatttcaa gtcttggcgc ccaaacatcg gcagtgaaaa      60
aaatgcttta                                                            70

<210> SEQ ID NO 10
<211> LENGTH: 70
<212> TYPE: DNA
<213> ORGANISM: Artificial
<220> FEATURE:
<223> OTHER INFORMATION: primer

<400> SEQUENCE: 10
atgtatacag acgttacggt catgtgggta gccgtgattt tatttactat ggcctggtga  60
tgatggcggg                                                          70

<210> SEQ ID NO 11
<211> LENGTH: 70
<212> TYPE: DNA
<213> ORGANISM: Artificial
<220> FEATURE:
<223> OTHER INFORMATION: primer

<400> SEQUENCE: 11
tcataccata caaaggcata ggtcagccc acaggttaaa aacaaagaaa gcagtgaaaa   60
aaatgcttta                                                          70

<210> SEQ ID NO 12
<211> LENGTH: 30
<212> TYPE: DNA
<213> ORGANISM: Artificial
<220> FEATURE:
<223> OTHER INFORMATION: primer

<400> SEQUENCE: 12
aagtgtataa attagacaag tagctatgcg                                    30

<210> SEQ ID NO 13
<211> LENGTH: 23
<212> TYPE: DNA
<213> ORGANISM: Artificial
<220> FEATURE:
<223> OTHER INFORMATION: primer

<400> SEQUENCE: 13
tcagaagaac tcgtcaagaa ggc                                           23

<210> SEQ ID NO 14
<211> LENGTH: 25
<212> TYPE: DNA
<213> ORGANISM: Artificial
<220> FEATURE:
<223> OTHER INFORMATION: primer

<400> SEQUENCE: 14
gtttatattg acgcggaatg ttgac                                         25

<210> SEQ ID NO 15
<211> LENGTH: 29
<212> TYPE: DNA
<213> ORGANISM: Artificial
<220> FEATURE:
<223> OTHER INFORMATION: primer

<400> SEQUENCE: 15
cattttaacc gtttaagtca acattccgc                                     29

<210> SEQ ID NO 16
<211> LENGTH: 27
<212> TYPE: DNA
<213> ORGANISM: Artificial
<220> FEATURE:
<223> OTHER INFORMATION: primer

<400> SEQUENCE: 16
actgagatgt tggaccatca aatcctg                                       27

<210> SEQ ID NO 17
<211> LENGTH: 26
<212> TYPE: DNA
<213> ORGANISM: Artificial
<220> FEATURE:
<223> OTHER INFORMATION: primer

<400> SEQUENCE: 17
gcgcatgcta gctgatctaa ctttac                                          26

<210> SEQ ID NO 18
<211> LENGTH: 30
<212> TYPE: DNA
<213> ORGANISM: Artificial
<220> FEATURE:
<223> OTHER INFORMATION: primer

<400> SEQUENCE: 18
ggtggccaat aaggcctgac ggcaatatgt                                      30

<210> SEQ ID NO 19
<211> LENGTH: 30
<212> TYPE: DNA
<213> ORGANISM: Artificial
<220> FEATURE:
<223> OTHER INFORMATION: primer

<400> SEQUENCE: 19
tcaggcctta ttggccacca gctacacaag                                      30

<210> SEQ ID NO 20
<211> LENGTH: 30
<212> TYPE: DNA
<213> ORGANISM: Artificial
<220> FEATURE:
<223> OTHER INFORMATION: primer

<400> SEQUENCE: 20
gcgaattcga ttaattctcc cgaactgttg                                      30

<210> SEQ ID NO 21
<211> LENGTH: 1506
<212> TYPE: DNA
<213> ORGANISM: Artificial
<220> FEATURE:
<223> OTHER INFORMATION: promoter

<400> SEQUENCE: 21
tgcagctcag tgcatgcacg ctcattgccc atcgctatcc ctgcctctcc tgctggcgct     60
ccccgggagg tgacttcaag gggaccgcag gaccacctcg ggggtggggg gagggctgca    120
cacgcggacc ccgctccccc tccccaacaa agcactgtgg aatcaaaaag gggggagggg    180
ggatggaggg gcgcgtcaca cccccgcccc acaccctcac ctcgaggtga gccccacgtt    240
ctgcttcact ctccccatct ccccccccctc cccaccccca attttgtatt tatttatttt    300
ttaattattt tgtgcagcga tgggggcggg ggggggggg gcgcgcgcca ggcggggcgg     360
ggcggggcca gggcggggc ggggcgaggc ggagaggtgc ggcggcagcc aatcagagcg    420
gcgcgctccg aaagtttcct tttatggcga ggcggcggcg gcggcggccc tataaaaagc    480
gaagcgcgcg gcgggcggga gtcgctgcgc gctgccttcg cccgtgccc cgctccgccg    540 ccgcctcgcg ccgcccgccc cggctctgac tgaccgcgtt actcccacag gtgagcgggc    600
gggacggccc ttctcctccg ggctgtaatt agcgcttggt ttaatgacgg ctcgtttctt    660

```
ttctgtggct gcgtgaaagc cttaaagggc tccgggaggg cccttttgtgc gggggggagc    720 ggctcggggg gtgcgtgcgt gtgtgtgtgc gtggggagcg ccgcgtgcgg ctccgcgctg    780
cccggcggct gtgagcgctg cgggcgcggc gcggggcttt gtgcgctccg cagtgtgcgc    840
gaggggagcg cggccggggg cggtgccccg cggtgcgggg ggggctgcga ggggaacaaa    900
ggctgcgtgc ggggtgtgtg cgtgggggg tgagcagggg gtgtgggcgc ggcggtcggg    960
ctgtaacccc cccctgcacc cccctccccg aagttgctga gcacgcccg gcttcgggtg    1020 cggggctccg tgcggggcgt ggcgcgggc tcgccgtgcc gggcgggggg tgcggcagg    1080 tgggggtgcc gggcggggcg gggccgcctc gggccgggga gggctcgggg gaggggcgcg   1140 gcggccccg agcgccggc ggctgtcgag gcgcggcgag ccgcagccat tgccttttat    1200
ggtaatcgtg cgagagggcg cagggacttc ctttgtccca aatctgtgcg gagccgaaat    1260
ctgggaggcg ccgccgcacc ccctctagcg ggcgcggggc gaagcggtgc ggcgccggca    1320
ggaaggaaat gggcggggag ggccttcgtg cgtcgccgcg ccgccgtccc cttctccatc    1380
tccagcctcg gggctgtccg caggggggacg gctgccttcg gggggggacgg ggcagggcgg    1440 ggttcggctt ctggcgtgtg accggcgggg tttatatctt cccttctctg ttcctccgca    1500
gccccc    1506

<210> SEQ ID NO 22
<211> LENGTH: 24
<212> TYPE: DNA
<213> ORGANISM: Artificial
<220> FEATURE:
<223> OTHER INFORMATION: primer

<400> SEQUENCE: 22
gtccactatg ccatgacata ggtg                                            24

<210> SEQ ID NO 23
<211> LENGTH: 20
<212> TYPE: DNA
<213> ORGANISM: Artificial
<220> FEATURE:
<223> OTHER INFORMATION: primer

<400> SEQUENCE: 23
gagcaacttc gagctgatcc                                                 20

<210> SEQ ID NO 24
<211> LENGTH: 24
<212> TYPE: DNA
<213> ORGANISM: Artificial
<220> FEATURE:
<223> OTHER INFORMATION: primer

<400> SEQUENCE: 24
gccagggaat ccagggaaaa agac                                            24

<210> SEQ ID NO 25
<211> LENGTH: 274
<212> TYPE: DNA
<213> ORGANISM: Artificial
<220> FEATURE:
<223> OTHER INFORMATION: promoter

<400> SEQUENCE: 25
tattttgtgc agcgatgggg gcggggggg gggggcgcg cgccaggcgg ggcggggcgg    60
```

```
ggcgaggggc ggggcggggc gaggcggaga ggtgcggcgg cagccaatca gagcggcgcg    120
ctccgaaagt ttccttttat ggcgaggcgg cggcggcggc ggccctataa aaagcgaagc    180
gcgcggcggg cgggagtcgc tgcgcgctgc cttcgccccg tgccccgctc cgccgccgcc    240
tcgcgccgcc cgccccggct ctgactgacc gcgt                                274

<210> SEQ ID NO 26
<211> LENGTH: 28
<212> TYPE: DNA
<213> ORGANISM: Artificial
<220> FEATURE:
<223> OTHER INFORMATION: primer

<400> SEQUENCE: 26
gcttgtgtag ctggttgacg gcaatatg                                        28

<210> SEQ ID NO 27
<211> LENGTH: 28
<212> TYPE: DNA
<213> ORGANISM: Artificial
<220> FEATURE:
<223> OTHER INFORMATION: primer

<400> SEQUENCE: 27
catattgccg tcaaccagct acacaagc                                        28

<210> SEQ ID NO 28
<211> LENGTH: 25
<212> TYPE: DNA
<213> ORGANISM: Artificial
<220> FEATURE:
<223> OTHER INFORMATION: primer

<400> SEQUENCE: 28
gcgcatgcca attgtctaat tccag                                           25

<210> SEQ ID NO 29
<211> LENGTH: 30
<212> TYPE: DNA
<213> ORGANISM: Artificial
<220> FEATURE:
<223> OTHER INFORMATION: primer

<400> SEQUENCE: 29
cccggccaat aaggccacag aaaaagcgcg                                      30

<210> SEQ ID NO 30
<211> LENGTH: 29
<212> TYPE: DNA
<213> ORGANISM: Artificial
<220> FEATURE:
<223> OTHER INFORMATION: primer

<400> SEQUENCE: 30
ctgtggcctt attggccggg atctggaac                                       29

<210> SEQ ID NO 31
<211> LENGTH: 23
<212> TYPE: DNA
<213> ORGANISM: Artificial
<220> FEATURE:
<223> OTHER INFORMATION: primer

<400> SEQUENCE: 31
gcgaattcat gtgctacgcc cag                                             23
```

<210> SEQ ID NO 32
<211> LENGTH: 25
<212> TYPE: DNA
<213> ORGANISM: Artificial
<220> FEATURE:
<223> OTHER INFORMATION: primer

<400> SEQUENCE: 32
cggtcgacac tcccaggggt gaagc                                      25

<210> SEQ ID NO 33
<211> LENGTH: 30
<212> TYPE: DNA
<213> ORGANISM: Artificial
<220> FEATURE:
<223> OTHER INFORMATION: primer

<400> SEQUENCE: 33
cggccaataa ggccaagaat gcattcggcc                                 30

<210> SEQ ID NO 34
<211> LENGTH: 30
<212> TYPE: DNA
<213> ORGANISM: Artificial
<220> FEATURE:
<223> OTHER INFORMATION: primer

<400> SEQUENCE: 34
tggccttatt ggccgccgta tgaattgcgc                                 30

<210> SEQ ID NO 35
<211> LENGTH: 25
<212> TYPE: DNA
<213> ORGANISM: Artificial
<220> FEATURE:
<223> OTHER INFORMATION: primer

<400> SEQUENCE: 35
gcgagctcct gcaaccacag accgc                                      25

<210> SEQ ID NO 36
<211> LENGTH: 28
<212> TYPE: DNA
<213> ORGANISM: Artificial
<220> FEATURE:
<223> OTHER INFORMATION: primer

<400> SEQUENCE: 36
cggtcgacat agaacgcgct tcatctaa                                   28

<210> SEQ ID NO 37
<211> LENGTH: 30
<212> TYPE: DNA
<213> ORGANISM: Artificial
<220> FEATURE:
<223> OTHER INFORMATION: primer

<400> SEQUENCE: 37
tggccaataa ggccgtttat tgtttattat                                 30

<210> SEQ ID NO 38
<211> LENGTH: 30
<212> TYPE: DNA
<213> ORGANISM: Artificial
<220> FEATURE:

```
<223> OTHER INFORMATION: primer

<400> SEQUENCE: 38
cggccttatt ggccaatctg attcatccaa                                          30

<210> SEQ ID NO 39
<211> LENGTH: 30
<212> TYPE: DNA
<213> ORGANISM: Artificial
<220> FEATURE:
<223> OTHER INFORMATION: primer

<400> SEQUENCE: 39
gcgagctccg cctaatcaca atcggtattg                                          30

<210> SEQ ID NO 40
<211> LENGTH: 27
<212> TYPE: DNA
<213> ORGANISM: Artificial
<220> FEATURE:
<223> OTHER INFORMATION: primer

<400> SEQUENCE: 40
ccgcatgcgc aactatatat gtcggtc                                             27

<210> SEQ ID NO 41
<211> LENGTH: 30
<212> TYPE: DNA
<213> ORGANISM: Artificial
<220> FEATURE:
<223> OTHER INFORMATION: primer

<400> SEQUENCE: 41
gggccaataa ggcccaaaag tacattttgt                                          30

<210> SEQ ID NO 42
<211> LENGTH: 30
<212> TYPE: DNA
<213> ORGANISM: Artificial
<220> FEATURE:
<223> OTHER INFORMATION: primer

<400> SEQUENCE: 42
gggccttatt ggcccaattt atttactatt                                          30

<210> SEQ ID NO 43
<211> LENGTH: 28
<212> TYPE: DNA
<213> ORGANISM: Artificial
<220> FEATURE:
<223> OTHER INFORMATION: primer

<400> SEQUENCE: 43
gcgaattctg gatatgatat accgttgc                                            28
```

DUCK ENTERITIS VIRUS AND THE USES THEREOF

CROSS-REFERENCE TO RELATED APPLICATION

This application is the U.S. national stage application of International Patent Application No. PCT/EP2017/065987, filed Jun. 28, 2017.

The Sequence Listing for this application is labeled "Seq-List.txt" which was created on Dec. 14, 2018 and is 12 KB. The entire content of the sequence listing is incorporated herein by reference in its entirety.

FIELD OF THE INVENTION

The present invention relates to novel viruses and the uses thereof. More particularly, the invention relates to novel Duck Enteritis Virus constructs and their use to express or deliver polypeptides of interest to animals, particularly poultry. The invention is particularly suited to vaccinate poultry against avian pathogens.

BACKGROUND OF THE INVENTION

Poultry meat and eggs are important food sources, whose consumption increases continually due to the growth of the human population and their great quality-price ratio. The recent epidemic of avian influenza focused the public opinion on poultry health as well as food safety and security, and poultry vaccine technology has become a worldwide concern.

Recombinant viruses expressing pathogen proteins are commonly used as poultry vaccines against targeted pathogens. Vaccines including such viruses induce expression of foreign pathogen proteins or fragments thereof within infected cells, which can subsequently induce a specific and protective humoral immunity as well as cell-mediated immunity.

In this regard, a number of viruses, in which a foreign gene derived from a pathogen has been integrated, have been developed to be used as viral-vectored vaccines. These viral vectors (or recombinant viruses) are based typically on avipox viruses, such as fowlpox (EP-A-0,517,292), herpes viruses, particularly HVT (e.g., WO-A-87/04463, 5,980, 906, 5,853,733), Newcastle disease virus (NDV) or avian adenoviruses. These recombinant avian viruses display variable levels of protection, depending on the disease and/or animal.

For instance, because Poxviruses, NDV, and adenoviruses do not persist in chickens, they are not considered the best candidates for long duration of immunity in chicken. Recombinant HVT expressing antigens have shown advantages and are currently commercialized for vaccination in chicken (e.g., Vectormune® IBD, Vectormune® ND, or Vectormune® LT).

Considering the increasing number and diversity of pathogens and the continuous growth of poultry consumption, there is, however, a need for alternative vaccination strategies and/or systems that may be used to cause effective protective immunity in poultry. There is in particular a need for effective systems to procure immunity in very young animals (3 days or less) or in ovo.

In this regard, new viral serotypes have been explored, with the aim to find alternative compatible viral vectors to improve vaccination in animals, particularly in poultry, allowing stable protein expression and effective protection.

WO2014/0036735 discusses the possible use of Duck Enteritis Virus in chicken. DEV naturally infects ducks or geese but has no known tropism for chicken. This document suggests that a DEV construct may be administered to 1-week-old chicken by intramuscular injection. In this document, however, only late administration is reported.

By conducting further experiments with DEV, the inventors have, however, found that such virus is lethal when administered to young chicken (3 days or less) or in ovo. Surprisingly, although administration to chicken of a wild-type DEV (or a DEV construct containing all native genes as proposed in WO2014/0036735) one week after hatch appears well tolerated, administration of such a construct at day 1 post-hatch or in ovo causes a very massive death of the animals (i.e., between 80-100%). Even more surprisingly, the inventors have been able to modify the structure of the DEV to produce DEV constructs that may be used in poultry, including at very early stage (3 days or less) or in ovo, and that can cause substantial and early stage protein expression in vivo. Such viruses thus represent novel potent vectors for vaccinating poultry.

SUMMARY OF THE INVENTION

The invention provides novel viral constructs suitable to express genes or proteins in vivo in animals, particularly poultry, including at very early stage (i.e., at day 3 post-hatch or earlier, as well as in ovo). Particularly, the invention provides novel DEVs obtained by inactivation of the US4 and US5 genes, and demonstrates that such DEVs are (i) attenuated in vivo, particularly in chicken, and (ii) are stable and capable of expressing foreign genes in a manner suitable for inducing protective immunity. Furthermore, these defective and attenuated DEVs retain a fast growth rate allowing production of high titers. Because such DEVs have no known natural tropism for e.g., chicken, the use of such DEV constructs for vaccinating chicken involves no risk of dissemination or contamination to non-vaccinated animals. Furthermore, chicken have no maternal antibodies or immunity against DEV and the viruses of the invention can be used to induce very early onset of immunity in vaccinated animals. Surprisingly, as indicated previously, while wild-type DEV is lethal in young chicken or in ovo, the DEVs of the invention are safe and can effectively express genes of interest in vivo. Such novel DEVs thus represent very potent vectors for vaccinating non-human animals, particularly poultry, and for conferring early protective immunity.

An object of the invention more particularly relates to a Duck Enteritis Virus (DEV), wherein said virus has inactive US4 and US5 genes. The invention indeed shows that by inactivating these genes, viable, stable and replicative DEVs can be obtained, and that such viruses may be used to create recombinant DEVs by insertion of foreign genetic material. The results further show that such foreign genetic material is highly expressed from such viruses upon cell infection, and that such expression remains stable over time. Moreover, and strikingly, while native DEV as well as many other deleted DEV constructs produced by the inventors were found pathogenic or lethal in young chicken (at day 3 post-hatch or earlier) and in ovo, inactivation of US4 and US5 generates attenuated viruses which can be used safely to express proteins and antigens into young animals, including in ovo. Such finding was totally surprising and offers high advantages and utility to the present viruses.

A further object of the invention thus relates to a Duck Enteritis Virus (DEV), wherein said virus has inactive US4 and US5 genes and comprises a foreign nucleic acid.

According to particular embodiments, the US4 and US5 genes are mutated, or deleted, or interrupted; and/or the foreign nucleic acid is located in replacement of all or part of the US4 and US5 gene sequences, and/or the foreign nucleic acid encodes an avian pathogen.

In a further particular embodiment, the DEV of the invention further comprises an inactive UL4, UL23, or US7 gene.

A further object of the invention is a nucleic acid molecule comprising the genome of a DEV having inactive US4 and US5 genes.

The invention further relates to a host cell comprising a DEV or a nucleic acid as defined above.

The invention also provides a method for producing or replicating a DEV as defined above, comprising infecting a competent cell with a nucleic acid molecule or with a DEV as defined above, and collecting the DEV.

The invention also relates to a method for making a recombinant DEV, comprising inserting a foreign nucleic acid in replacement of all or at least 20% of the US4 and US5 gene sequences.

The invention also provides a composition comprising a DEV, a nucleic acid, or a host cell as defined above, a pharmaceutically or veterinary acceptable excipient or carrier and, optionally, an adjuvant.

The invention also provides a vaccine comprising a DEV, a nucleic acid, or a host cell as defined above, a pharmaceutically or veterinary acceptable excipient or carrier and, optionally, an adjuvant.

A further object of the invention relates to a composition, DEV, nucleic acid or host cell as defined above, for use to vaccinate or immunize avians, particularly poultry, more particularly chicken, more particularly young poultry (at Day 3 post-hatch or earlier or in ovo).

A further object of the invention relates to a composition, DEV, nucleic acid or host cell as defined above, for use to induce protective immunity in avians, particularly poultry, more particularly chicken, more particularly young poultry (at Day 3 post-hatch or earlier or in ovo).

The invention also relates to a method of vaccinating a non-human animal, particularly poultry, more particularly chicken, more particularly young poultry (at Day 3 post-hatch or earlier or in ovo), comprising administering to said non-human animal a composition, or virus as defined above.

A particular object of the invention is a method of vaccinating poultry comprising in ovo administration of a composition, or virus as defined above.

Another particular object of the invention is a method of vaccinating poultry comprising administration of a composition, or virus as defined above at Day 1 (i.e., within about 24 hours) post-hatch.

In a further aspect, the invention provides a method for inducing an immunogenic or protective response in a non-human animal against one or more avian pathogens comprising administering to said non-human animal, particularly poultry, more particularly chicken, more particularly young poultry (at Day 3 post-hatch or earlier or in ovo), a composition, vaccine or virus as defined above.

The viruses or compositions of the invention may be administered by any route. Preferably, they are administered in ovo or by subcutaneous (e.g., s.c.) injection 1 or 2 days post-hatch, to confer immunity very early.

The invention further provides a vaccination kit for immunizing an avian, which comprises the following components:

a. an effective amount of a composition as above, and
b. a means for administering said composition to said avian.

The invention may be used for expressing a polypeptide in any animal, preferably for the vaccination of an avian, and it is suitable for expressing one or several polypeptides or peptides, particularly immunogenic peptides of avian pathogens.

LEGEND TO THE FIGURES

DETAILED DESCRIPTION OF THE INVENTION

Figure 1:
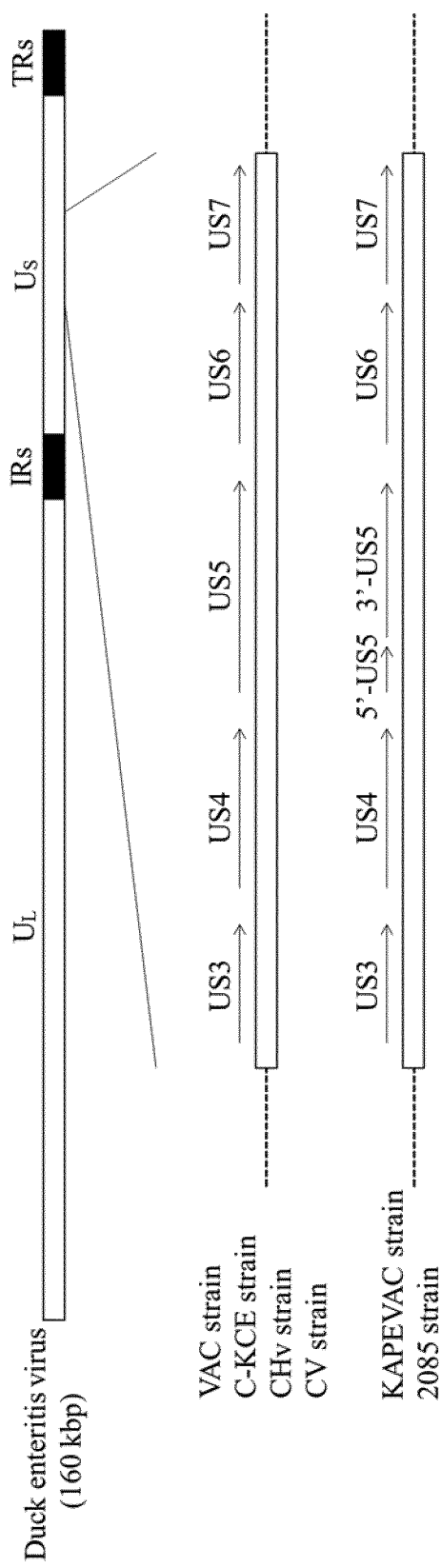
FIG. 1 illustrates a schematic diagram of the Duck enteritis virus (DEV) genome and the location of the US genes.

The present invention generally relates to attenuated DEVs which comprise foreign gene sequence(s). The present invention also relates to compositions comprising such DEVs, as well as to the use thereof for vaccination of animals, particularly poultry, more particularly young poultry (at Day 3 post-hatch or earlier, or in ovo).

The present disclosure will be best understood by reference to the following definitions:

Definitions

The term "virus" designates in particular a viral particle comprising a nucleic acid molecule (e.g., a genome) encapsulated in a capsid or capsule. The term "virus" also designates a viral vector or an isolated viral genome.

The term "recombinant" designates a molecule which has been created, designed or modified using genetic technologies. In relation to a virus, the term "recombinant" more specifically designates a virus whose genome (or whose ancestor's genome) has been modified by insertion or deletion of at least one nucleic acid sequence.

The term "foreign nucleic acid" in relation to a virus designates a nucleic acid which is not found naturally in the genome of the virus, or which is found naturally in said genome but in a different form or at a different position.

In the present description, the term "nucleic acid" or "nucleic acids" designates any nucleic acid molecule or sequence such as deoxyribonucleotide (DNA) or ribonucleotide (RNA), which may be e.g., single- or double-stranded. Nucleic acids may comprise an ORF or not. Nucleic acid molecules may be produced by techniques known per se in the art such as by artificial synthesis, recombinant technology, enzymatic technology, replication in host cells, or combinations thereof.

A "gene" designates a nucleic acid molecule or sequence which comprises an open reading frame encoding a product, such as a polypeptide (e.g., a peptide, protein, etc.) or an RNA.

Within the context of the invention, a DEV having an "inactive" gene designates a DEV that cannot express a functional protein or RNA encoded by said gene. An inactive US4 gene thus designates a mutated, a deleted, and/or an interrupted US4 gene that cannot encode a wild-type US4 protein. An inactive US5 gene designates a mutated, a deleted, and/or an interrupted US5 gene that cannot encode a wild-type US5 protein. Where the US5 gene contains a 5'US5 and a 3'US5 coding sequence, an inactive US5 designates a mutated, a deleted, and/or an interrupted US5 gene that cannot encode any wild-type protein encoded by said 5'US5 and 3'US5 coding sequences, e.g., both the 5'US5 and the 3'US5 contain a mutation or deletion or interruption.

The term "attenuated" as used herein refers to a virus which essentially does not cause illness in an animal model. An attenuated virus can typically replicate in a host without causing death thereof. An attenuated virus more particularly designates a virus which is not virulent in embryos when injected at a dose of $1 \times 10^3$ plaque forming unit (pfu)/egg. Most preferred attenuated viruses are safe at a dose of $1 \times 10^3$ pfu/egg in at least 70% injected eggs, more preferably in at least 80% injected eggs, even more preferably in at least 90%, 95% 97%, 98%, 99% or more. Attenuated viruses of the invention are also safe for injection post-hatch, including at Day 0 (i.e., between 0.1 and 48 hours post-hatch).

The term "avian" is intended to encompass all kinds of avians such as birds of the class of Ayes, i.e., vertebrate animals which are feathered, winged, bipedal, endothermic, and egg-laying. In the context of the invention, avians or avian species refer more particularly to birds with economical and/or agronomical interests, such as poultry, more preferably chickens and turkeys; or ornamental birds such as swans and psittacines.

The term "vaccine" as used herein designates an agent which may be used to cause, stimulate or amplify an immune response in an organism.

An "immune response" designates the development in a host of a cellular and/or antibody-mediated immune response to a composition or vaccine of interest. Usually, an "immune response" includes the production of antibodies, B cells, helper T cells, and/or cytotoxic T cells, directed specifically to an antigen or antigens included in the composition or vaccine of interest. Preferably, the immune response is protective such that resistance to new infection will be enhanced and/or the clinical severity of the disease reduced.

The term "in ovo" administration or injection generally means inoculation or injection in the embryo contained in an egg. In ovo injection is preferably conducted anytime between Day 5 and Day 1 before hatch.

Duck Enteritis Virus

Duck Enteritis Virus (DEV), also known as a duck viral enteritis virus (DVEV), naturally infects ducks and geese. The full nucleotide sequence of DEV has been determined and is available online (see for instance JQ673560). The viral genome contains about 162 Kb, encoding nearly 80 distinct proteins. Several serotypes and strains of DEV have been isolated, such as the Jansen strain, the CSC strain, the CHv strain, the VAC strain, and the 2085 strain. The complete sequences of several DEV strains are available in Genbank, such as the VAC strain: ID EU082088.2; the Anatid isolate C-KCE: ID KF263690.1; the Anatid strain CHv: ID JQ647509.1; the Anatid strain 2085: ID JF999965; the Anatid strain CV: ID KJ549663.1 or the Anatid strain CSC: ID JQ673560.1.

DEV remains poorly characterized and its use as a vector to express genes has not been deeply investigated. For instance, Liu et al (2013) and WO2014/0036735 have attempted to use a recombinant DEV for expressing genes into chicken. They have utilized a DEV construct wherein a nucleic acid has been cloned between the US7 and US8 genes of the viral genome, without altering native gene expression. Although it is reported that such a construct may be transferred by intramuscular injection into 1-week-old chicken, there is, however, no disclosure in this document or in any other prior art document of any possible use of DEV for in ovo vaccination of poultry, or for vaccination of young poultry, i.e., at Day3 post-hatch or before, particularly at Day 1 or Day 2 post-hatch.

By conducting further experiments with DEV, the inventors surprisingly found that this virus is lethal when administered to young chicken (3 days or less) or in ovo. Surprisingly, although administration to chicken of a wild-type DEV (or a DEV construct containing all native genes as proposed in WO2014/0036735) one week after hatch appears well tolerated, administration of such a construct at day 1 post-hatch or in ovo causes a very massive death of the animals (i.e., between 80-100%), as reported in example 1.

Even more surprisingly, the inventors have been able to modify the structure of the DEV to produce DEV constructs that may be used in poultry, including at very early stage (3 days or less) or in ovo, and that can cause substantial and early stage protein expression in vivo. More particularly, the present inventors conducted further research with DEV and generated various recombinants with different gene deletions or alterations. The inventors have surprisingly discovered that, by inactivation of both the US4 and US5 genes, recombinant DEVs can be obtained which are (i) attenuated in vivo, particularly in chicken, and (ii) stable and capable of expressing foreign genes in a manner suitable for inducing protective immunity. The results further show that such foreign genetic material is highly expressed from such viruses upon cell infection, and that such expression remains stable over time. Moreover, and strikingly, inactivation of US4 and US5 generates attenuated DEVs which can be used safely to express proteins or antigens into young poultry and in ovo, while DEVs having an inactive US4 gene only or an inactive US5 gene only remain pathogenic or lethal in young chicken (below age of 3 days or in ovo). Because DEV has no known natural tropism for e.g., chicken, the use of DEV constructs of the invention for vaccinating chicken involves no risk of dissemination or contamination to non-vaccinated animals. Furthermore, chicken have no maternal antibodies or immunity against DEV and the viruses of the invention can be used to induce very early onset of immunity in vaccinated animals.

An object of the invention thus relates to a Duck Enteritis Virus (DEV), wherein said virus has inactive US4 and US5 genes.

A further object of the invention relates to a Duck Enteritis Virus (DEV), wherein said virus has inactive US4 and US5 genes and contains a foreign nucleic acid.

The DEVs of the invention may be prepared from any DEV species or strain. A number of strains of DEV have been reported, which are available from public collections, such as the Jansen strain, the VAC strain (ID EU082088.2), the C-KCE strain (ID KF263690.1), the CHv strain (ID JQ647509.1), the 2085 strain (ID JF999965), the CV strain (ID KJ549663.1) or the CSC strain (ID JQ673560.1).

In a preferred embodiment, the DEV of the invention is derived or prepared from a parental strain selected from the Jansen strain or the CSC strain, or any DEV strain having at least 90% sequence identity to the Jansen strain or CSC strain, more preferably at least 95%, at least 96%, at least 97%, at least 98%, or at least 99%.

The invention shows that, by inactivating (i.e., rendering non-functional or deleting) the US4 and US5 genes, it is possible to generate attenuated DEVs that are safe even when injected in ovo or in young poultry, and that can replicate and express proteins in poultry. In particular, as shown in the examples, DEV constructs having inactive US4 and US5 genes are stable, can be replicated in culture, and can be safely administered to poultry eggs or young poultry. Such viruses may thus be used to produce recombinant DEVs containing foreign nucleic acid material, particularly antigenic-coding genes, to express such genes in poultry.

Within the context of the invention, a DEV having an inactive gene designates a DEV that cannot express a functional protein or RNA encoded by said gene. An inactive gene thus particularly designates a mutated, a deleted, and/or an interrupted gene that cannot encode a wild-type protein.

In a particular embodiment, the gene is inactive as a result of one or several mutations in the coding sequence, particularly point mutations in the coding sequence that prevent expression of a full length protein. Such mutations may introduce a stop or non-sense codon in the sequence, or cause substitution of essential amino acid residue(s) in the encoded protein, resulting in an inactive protein.

In another embodiment, the gene is inactive as a result of a deletion of at least a portion of the (coding) sequence of said gene, more particularly of at least 20% of the (coding) sequence of the gene, more preferably at least 30%, at least 40%, at least 50%, at least 60%, at least 70%, at least 80%, or at least 85%, up to 100%. In a preferred example, the DEV of the invention has a deletion of at least 300 bp of the (coding sequence of the) gene to be inactivated. Such deletion removes coding sequence and thus prevents expression of a wild type protein, or even of any protein.

In this regard, a particular embodiment of the invention relates to a Duck Enteritis Virus (DEV), wherein said virus has deletions in/of the US4 and US5 genes, particularly in/of the coding sequence of the US4 and US5 genes.

The US4 and US5 genes of DEV are predicted to encode proteins. However, the actual function of these genes remains unclear. Up to the present invention, the ability to generate US4-US5 doubly defective DEV viruses was not known, and the ability of such DEV viruses to replicate and express foreign genes, without being lethal in avians, was totally unknown.

The US4 gene is typically composed of 1380 bp of a DEV genome and encodes a protein comprising approximately 459 amino acid residues. US4 is highly conserved between DVE strains. By reference to a CSC strain, the US4 gene corresponds to nt141123 to nt142502 of the genome. It is understood that the skilled artisan may easily identify the exact location of the US4 gene in any DEV strain using the information contained in the present application and general common knowledge, or by sequence alignment. In a particular DEV of the invention, at least 20% of the US4 (coding) gene sequence is deleted, more preferably at least 30%, at least 40%, at least 50%, at least 60%, at least 70%, at least 80%, at least 90%, up to 100%. In a preferred example, the DEV of the invention has a deletion of at least 500 bp of the US4 (coding) gene sequence, more preferably at least 600, 700, 800, 900, 1000, or more. In a specific embodiment, a DEV of the invention has a deletion spanning at least nt 200-1000 of the US4 gene sequence, more preferably at least nt150-1150, even more preferably at least nt100-1300. In a specific example, a DEV of the invention has a deletion of nt51 to nt1330 (i.e., above 90%) of the US4 gene sequence. In another particular embodiment, a DEV of the invention has a deletion of all of the US4 gene sequence (nt1-1380).

The US5 gene of DEV encodes a glycoprotein, the function of which remains unknown. In most DEV strains (e.g., VAC, CSC, C-KCE, CHv, CV), the US5 gene is composed of approximately 1620 bp and encodes a protein of approximately 539 amino acid residues. In some DEV strains, such as a 2085 strain and a Jansen (or Kapevac) strain, the US5 gene contains two shorter coding regions: 5'US5 of approximately 396 bp and 3'US5 of approximately 1197 bp, separated by a small intergenic region of approximately 25 bp (see FIG. 1). By reference to a CSC strain, the US5 gene corresponds to nt142662 to nt144281 of the genome. It is understood that the skilled artisan may easily identify the exact location of the US5 gene in any DEV strain using the information contained in the present application and general common knowledge, or by sequence alignment. In a particular DEV of the invention, at least 20% of the US5 (coding) gene sequence is deleted, more preferably at least 30%, at least 40%, at least 50%, at least 60%, at least 70%, at least 80%, at least 90%, up to 100%. In a preferred example, the DEV of the invention has a deletion of at least 500 bp of the US5 (coding) gene sequence, more preferably at least 600, 700, 800, 900, 1000, or more. In a specific embodiment, a DEV of the invention has a deletion spanning at least nt 200-1000 of the US5 gene sequence, more preferably at least nt100-1100, even more preferably at least nt80-1120. When the US5 gene contains two ORFs, it is preferred that both ORFs are inactive. In this regard, where the DVE is prepared from a viral strain having a US5 gene sequence containing a single ORF, the DVE preferably comprises a deletion of at least 90% of said ORF, such as a deletion of at least nt51 to nt1570 of the US5 gene sequence, more particularly a deletion of all of the US5 gene. Where the DVE is prepared from a viral strain having a US5 gene sequence containing two ORFs, the DVE preferably comprises a deletion of at least 90% of each of said ORFs, more preferably a deletion comprising at least 90% of the first ORF, the full intergenic region, and at least 90% of the second ORF.

In a specific embodiment, a DEV of the invention has a deletion of a contiguous region spanning at least a portion of the US4 gene, the entire US4-US5 intergenic region, and a portion of the US5 gene.

In a further specific embodiment, the DVE comprises a deletion of a nucleotide region comprising at least 50% of the US4 gene, all of the intergenic region between the US4 gene and the US5 gene, and at least 50% of the US5 gene.

In a more preferred embodiment, the DVE comprises a deletion of a nucleotide region comprising all of the US4 gene, all of the intergenic region between the US4 gene and the US5 gene, and all of the US5 gene. A specific example of such a construct is e.g., DEV/US4US5/BacVP2).

As indicated above, the DVEs of the invention can contain one or several foreign nucleic acid of interest. The foreign nucleic acid is generally under control of a transcriptional promoter. Preferably the promoter is cloned with the foreign nucleic acid. The promoter may be any natural or synthetic promoter, derived from cellular or viral genes. Examples of suitable promoters include, for instance, the chicken beta-actin (Bac) promoter or a derivative thereof such as Coa5, the Pec promoter, the Murine Cytomegalovirus (Mcmv) immediate-early (ie)1 promoter, the Human Cytomegalovirus promoter (Hcmv), the Simian virus (SV) 40 promoter, and the Rous Sarcoma virus (RSV) promoter, or any fragments thereof which retain a promoter activity. In a variant, the foreign nucleic acid is cloned downstream and under transcriptional control of a transcriptional promoter present in the DEV genome.

In a particular embodiment, the foreign nucleic acid is located in the US4 gene sequence of the DEV viral genome, either in addition to the existing US4 gene sequence (thus rendering the gene inactive by interrupting the gene sequence), or in replacement of a deleted sequence of the US4 gene, or in a mutated US4 gene sequence. In an alternative embodiment, the foreign nucleic acid is located in the US5 gene sequence of the DEV viral genome, either in addition to the existing US5 gene sequence (thus rendering the gene inactive by interrupting the gene sequence), or in replacement of a deleted sequence of the US5 gene, or in a mutated US5 gene sequence.

In a preferred embodiment, the DEV of the invention has a deletion in the US4 and US5 gene sequences, and contains a foreign nucleic acid located in place of the deleted nucleotides.

In an alternative embodiment, the DEV of the invention has inactive US4 and US5 genes and contains a foreign nucleic acid located in a different cloning site, such as in a site selected from the UL4 gene, the UL44 gene, the UL27-UL26 intergenic region, the UL23 gene, the UL45-UL46 intergenic region, the UL50-UL51 intergenic region, the US7 gene, the US7-US8 intergenic region, or the US10 gene. In this case, the foreign nucleic acid may be cloned in replacement of all or part of said gene, or it may be inserted within said gene.

Furthermore, the DEVs of the invention may comprise several foreign nucleic acids. In this regard, the several foreign nucleic acids may be inserted in the same position in the virus, e.g., in the US4/US5 region as described above, under the control of a single or several distinct promoters. Alternatively, the foreign nucleic acids may be inserted into distinct cloning site of the virus, such as one in the US4/US5 region as described above, and at least one in a distinct region preferably selected from the UL4 gene, the UL44 gene, the UL27-UL26 intergenic region, the UL23 gene, the UL45-UL46 intergenic region, the UL50-UL51 intergenic region, the US7 gene, the US7-US8 intergenic region, or the US10 gene, typically in replacement of all or part of the endogenous gene or region.

The UL4 gene is typically composed of 717 bp of a DEV genome. By reference to a CSC strain, the UL4 gene corresponds to nt112845 to nt113561 of the genome. It is understood that the skilled artisan may easily identify the exact location of the UL4 gene in any DEV strain using the information contained in the present application and general common knowledge, or by sequence alignment. In a particular embodiment, the invention relates to a Duck Enteritis Virus (DEV), wherein said virus has inactive US4, US5 and UL4 genes. More particularly, the invention relates to a DEV, wherein said virus has inactive US4, US5 and UL4 genes and comprises a first foreign nucleic acid cloned into the US4/US5 genes or in the UL4 gene, preferably in replacement of at least 20% of said gene. In a particular DEV of the invention, at least 20% of the UL4 gene sequence is deleted, more preferably at least 30%, at least 40%, at least 50%, at least 60%, at least 70%, at least 80%, at least 90%, up to 100%. In a preferred example, the DEV of the invention has a deletion of at least 500 bp of the UL4 gene sequence, more preferably at least 600, 700, 800, 900, 1000, or more.

The UL23 gene is typically composed of 1077 bp of a DEV genome. By reference to a CSC strain, the UL23 gene corresponds to nt77997 to nt79073 of the genome. It is understood that the skilled artisan may easily identify the exact location of the UL23 gene in any DEV strain using the information contained in the present application and general common knowledge, or by sequence alignment. In a particular embodiment, the invention relates to a Duck Enteritis Virus (DEV), wherein said virus has inactive US4, US5 and UL23 genes. More particularly, the invention relates to a DEV, wherein said virus has inactive US4, US5 and UL23 genes and comprises a first foreign nucleic acid cloned into the US4/US5 genes or in the UL23 gene, preferably in replacement of at least 20% of said gene. In a particular DEV of the invention, at least 20% of the UL23 gene sequence is deleted, more preferably at least 30%, at least 40%, at least 50%, at least 60%, at least 70%, at least 80%, at least 90%, up to 100%. In a preferred example, the DEV of the invention has a deletion of at least 500 bp of the UL23 gene sequence, more preferable at least 600, 700, 800, 900, 1000, or more. In a specific embodiment, a DEV of the invention has a deletion spanning at least nt 200-900 of the UL23 gene sequence, more preferably at least nt100-1000, even more preferably at least nt80-1000. In a specific example, a DEV of the invention has a deletion of nt51 to nt1027 (i.e., about 90%) of the UL23 gene sequence.

The US7 gene is typically composed of 1116 bp of a DEV genome. By reference to a CSC strain, the US7 gene corresponds to nt145769 to nt146884 of the genome. It is understood that the skilled artisan may easily identify the exact location of the US7 gene in any DEV strain using the information contained in the present application and general common knowledge, or by sequence alignment. In a particular embodiment, the invention relates to a Duck Enteritis Virus (DEV), wherein said virus has inactive US4, US5 and US7 genes. More particularly, the invention relates to a DEV, wherein said virus has inactive US4, US5 and US7 genes and comprises a first foreign nucleic acid cloned into the US4/US5 genes or in the US7 gene, preferably in replacement of at least 20% of said gene. In a particular DEV of the invention, at least 20% of the US7 gene sequence is deleted, more preferably at least 30%, at least 40%, at least 50%, at least 60%, at least 70%, at least 80%, at least 90%, up to 100%. In a preferred example, the DEV of the invention has a deletion of at least 500 bp of the US7 gene sequence, more preferably at least 600, 700, 800, 900, 1000, or more.

The invention also relates to a DEV, wherein said virus comprises a first foreign nucleic acid cloned into the US4/US5 genes and a second foreign nucleic acid cloned in an intergenic region located between UL27 and UL26 genes, preferably in replacement of at least 20% of said gene. The invention also relates to a DEV, wherein said virus comprises inactive US4 and US5 genes, and wherein said virus comprises a foreign nucleic acid cloned in an intergenic region located between UL27 and UL26 genes. By reference to a CSC strain, the intergenic region located between UL27 and UL26 corresponds to nt72195 to nt72646 of the genome. Cloning may be performed at any position within such domain, more preferably between nt72300 and nt72500, furthermore preferably between nt72350 and nt72450. In a specific embodiment, cloning is performed between nt72431 and nt72432.

The invention also relates to a DEV, wherein said virus comprises an inactive UL4 gene, and wherein said virus comprises a foreign nucleic acid cloned in an intergenic region located between US7 and US8 genes, or between UL45 and UL46 genes, or between UL50 and UL51 genes. By reference to a CSC strain, the intergenic region located between UL45 and UL46 corresponds to nt25132 to nt25352 of the genome. Cloning may be performed at any position within such domain, more preferably between nt25200 and nt25300. In a specific embodiment, cloning is performed between nt25275 and nt25276. By reference to a CSC strain, the intergenic region located between UL50 and UL51 corresponds to nt15914 to nt16063 of the genome. Cloning may be performed at any position within such domain, more preferably between nt15970 and nt16010. In a specific embodiment, cloning is performed between nt15979 and nt15980.

Virus construction and cloning may be accomplished by techniques know per se in the art. Gene cloning and plasmid construction are well known to one person of ordinary skill in the art and may be essentially performed by standard molecular biology techniques (Molecular Cloning: A Laboratory Manual. 4th Edition, Cold Spring Harbor Laboratory, Cold Spring Harbor, N.Y., USA, 2012). Typically, the recombinant viruses may be prepared by homologous recombination between the viral genome and a construct (e.g., a homology plasmid) comprising the nucleic acid to be inserted, flanked by nucleotides from the insertion site to allow recombination. Cloning can be made with or without deletion of endogenous sequences. In a particular embodiment, the recombinant sequence is cloned in replacement of at least part of a sequence of the genome, such as at least 50 nucleotides or more. Such deletion increases the cloning capacity of the virus.

For construction, a sequence containing the targeted insertion region is typically first cloned into a suitable vector to produce a homology vector. Examples of vectors include plasmids, such as pBR322, pBR325, pBR327, pBR328, pUC18, pUC19, pUC7, pUC8, or pUC9; phages such as lambda phage and M13 phage; or cosmids such as pHC79. The target region sequence is integrated into the vector by conventional cloning methods. The target region sequence used is preferably of sufficient length so as to allow subsequent in vivo homologous recombination with a DEV viral genome. Preferably, the cloned target region sequence shall have at least approximately 100 nucleotides in length, typically above 300, such as between 500 and 2000 nucleotides. The foreign nucleic acid (which typically contains a gene and a promoter) is then inserted into the target region cloned in the vector. Insertion shall be made preferably in a manner that leaves a portion of sequence of the target region on each side of the cloned insert of a length sufficient to allow homologous recombination (e.g. of at least 50 nucleotides, preferably of at least 100 nucleotides). The foreign nucleic acid can be introduced into the cloned target region by classical techniques such as restriction enzyme and ligation procedures. If appropriate, mutation(s) may be introduced at a specific site of the target region to create a new cleavage site for a restriction enzyme. Conventional mutagenesis techniques well known by a person skilled in the art may be used for that purpose, such as e.g., in vitro mutagenesis or PCR. Homology vectors in which the foreign nucleic acid has been inserted into the target region may then be introduced into a DEV-infected cell or DEV genome-transfected cells using known techniques such as electroporation, calcium phosphate, lipofectin-based method, or the like. The recombinant viruses are thereby produced by recombination in said cells between the virus and the vector. The resulting recombinant virus may be selected genotypically or phenotypically using known techniques, e.g., by hybridization, sequencing, PCR or a functional assay to detect any product encoded by the foreign nucleic acid, as described in the examples. The selected recombinant virus can be cultured on a large scale in cell culture after which, recombinant viruses can be collected.

Foreign Gene

The DEV of the invention may contain any foreign nucleic acid, preferably any foreign gene. The foreign gene may encode any product of interest such as RNAs or biologically active and/or immunogenic (e.g., antigenic) proteins, polypeptides or peptides. In a preferred embodiment, the foreign gene encodes an antigen, even more preferably a peptide or polypeptide derived from an antigen of a pathogenic organism capable of causing an infection in an animal, particularly an avian. Examples of pathogens that cause infection in avian include viruses, bacteria, fungi, protozoa, etc. The immunogenic (poly)peptide may preferably be (derived from) a surface protein, a secreted protein, or a structural protein of said pathogen, or fragments thereof. The polypeptide can be derived from any source, e.g., viral, prokaryotic, eukaryotic or synthetic.

In a preferred embodiment, the foreign gene encodes an antigenic peptide of a bird pathogenic agent.

Specific examples of pathogenic agents include, without limitation, avian influenza virus, avian paramyxovirus type 1, also called Newcastle disease virus (NDV), avian metapneumovirus, Marek's disease virus, Gumboro disease virus, also called infectious bursal disease virus (IBDV), Infectious laryngotracheitis virus (ILTV), Infectious bronchitis virus (IBV), *Escherichia coli, Salmonella* species, *Pasteurella multocida, Riemerella anatipestifer, Ornithobacterium rhinotracheale, Mycoplasma gallisepticum, Mycoplasma synoviae, Mycoplasmas* microorganisms infecting avian species or coccidian.

Preferentially, the foreign gene encodes an antigen selected from the F protein of NDV, the HN protein of NDV, the VP2 protein of IBDV, the gB protein of ILTV, the 40K protein of *Mycoplasma galisepticum*, or the surface protein hemagglutinin (HA) of the avian influenza virus, or immunogenic fragments thereof. Within the context of the invention, the term "fragment" of a protein designates preferably a fragment comprising at least 5 consecutive amino acid residues of said protein, even more preferably from 5-100. In a preferred embodiment, such a fragment comprises at least one epitope and/or is immunogenic in vivo, i.e., can cause production of antibodies that bind the full length protein.

Specific examples of immunogenic peptides include, for instance, a peptide comprising amino acid residues 1-453 of VP2, 1-469 of gB, or 1-540 of F.

Preferred DEVs

A preferred DEV of the invention comprises a deletion of the entire US4 and US5 genes.

A particular DEV of the invention comprises a deletion of a contiguous region comprising at least 50% of the nucleotide sequence of the US4 gene sequence, the entire US4-US5 intergenic region, and at least 50% of the nucleotide sequence of the US5 gene sequence.

A further particular DEV of the invention comprises a deletion of a contiguous region comprising all of the nucleotide sequence of the US4 gene sequence, the entire US4-US5 intergenic region, and all of the nucleotide sequence of the US5 gene sequence.

In a preferred DEV of the invention, the foreign nucleic acid encodes an avian antigen, more preferably a VP2, FIN or F protein or an immunogenic fragment thereof.

Another preferred DEV of the invention comprises inactive US4 and US5 genes and at least one further deletion selected from:
 a deletion of at least nt100-nt1000 of the US7 gene sequence,
 a deletion of at least nt100-nt1200 of the UL4 gene sequence, and/or
 a deletion of at least nt100-nt1000 of the UL23 gene sequence.

Another preferred DEV of the invention comprises inactive US4 and US5 genes and at least one foreign nucleic acid cloned into a distinct region preferably selected from the UL4 gene, the UL44 gene, the UL27-UL26 intergenic region, the UL23 gene, the UL45-UL46 intergenic region, the UL50-UL51 intergenic region, the US7 gene, the US7-US8 intergenic region, or the US10 gene.

Nucleic Acids

The invention also relates to a nucleic acid molecule comprising the genome of a DEV having inactive US4 and US5 genes. Such nucleic acid may be single- or double-stranded, DNA or RNA. In a particular embodiment, the nucleic acid is a DNA molecule containing the genome of a DEV as defined above.

The nucleic acid may be in free form, or in a vector such as a plasmid, BAC, and the like. The nucleic acid may be isolated, or contained in a host cell.

Cell Cultures

The recombinant viruses of the present invention may be propagated in any competent cell cultures. After required growth of the viruses is achieved, the cells may be detached from the wells using a scraper or with trypsin and the infected cells may be separated from the supernatant by centrifugation.

Examples of competent cells include CEF, embryonated egg, chicken kidney cell, and the like. The cells or viruses may be cultured in a culture medium such as Eagle's MEM, Leibowitz-L-15/McCoy 5A (1:1 mixture) culture medium at about 37° C. for 3 to 6 days. The infected cells are typically suspended in a culture medium containing 10% dimethyl sulfoxide (DMSO) and stored frozen under liquid nitrogen.

Compositions and Vaccines

The invention also relates to compositions, such as vaccines, which comprise one or more DEVs of the invention.

Compositions and vaccines of the invention may comprise the DEVs in a pharmaceutically or veterinary acceptable vehicle or excipient. The compositions and vaccines may, in addition or alternatively, comprise a suitable adjuvant.

The compositions and vaccines according to the present invention may comprise a suitable solvent, such as for example an aqueous buffer or a phosphate buffer. Preferably, the compositions and vaccines also comprise additives, such as a stabilizing agent, a preservative, a coloring agent, a surfactant, etc.

For instance, the compositions or vaccines of the present invention may be formulated with one or more further additives to maintain isotonicity, physiological pH and stability, for example, a buffer such as physiological saline (0.85%), phosphate-buffered saline (PBS), citrate buffers, Tris(hydroxymethyl aminomethane (TRIS), Tris-buffered saline and the like, or an antibiotic, for example, neomycin or streptomycin, etc.

In a particular embodiment, the composition of the invention comprises a preservative.

In another particular embodiment, the composition of the invention comprises a solubilizing agent.

In another particular embodiment, the composition of the invention comprises an adjuvant. Adjuvants may be obtained from any of a number of sources including various proteins and peptides derived from animals (e.g., hormones, cytokines, co-stimulatory factors), and novel nucleic acids derived from viruses and other sources (e.g., double stranded RNA, CpG), and the like which, alone or in combination(s), are sufficient to enhance the immune response.

The compositions of the invention may be liquid (solutions, suspensions, emulsions) or solid (powder, gel, paste, oil) and they may be formulated for any administration route. Preferably, they are formulated for injection, such as in ovo injection or for e.g., intravenous, subcutaneous, intramuscular, intraorbital, intraocular, intradermal, and/or intraperitoneal injection. Alternatively, they may be formulated for oral, ocular (e.g., by eyedrop), intranasal, or oculo-nasal administration, e.g., using aerosol or spray.

Each vaccine dose may contain a suitable dose sufficient to elicit a protective immune response in avian species. Optimization of such dose is well known in the art. The amount of antigen per dose may be determined by known methods using antigen/anti-body reactions, for example by the ELISA method.

The vaccines of the invention can be administered as single doses or in repeated doses, depending on the vaccination protocol.

In a particular embodiment, the invention relates to a vaccine comprising a virus, nucleic acid or cell as defined above and a suitable excipient or adjuvant.

In a further particular embodiment, the invention relates to a vaccine comprising a liquid composition of a virus, nucleic acid or cell as defined above and a suitable excipient or adjuvant.

The present invention further relates to the use of the virus, composition, vaccine, nucleic acid or cell as described above for immunizing avian species, such as poultry, and to method of immunizing avian species by administering an immunologically effective amount of the virus, composition, vaccine, nucleic acid or cell as described above.

A further object of the invention relates to a composition, DEV, nucleic acid or host cell as defined above, for use to vaccinate or immunize avians, particularly poultry, more particularly chicken, more particularly young poultry (at Day 3 post-hatch or earlier) or in ovo.

A further object of the invention relates to a composition, vaccine, DEV, nucleic acid or host cell as defined above, for use to induce protective immunity in avians, particularly poultry, more particularly chicken, more particularly young poultry (at Day 3 post-hatch or earlier) or in ovo.

The invention also relates to a method of vaccinating a non-human animal, particularly poultry, more particularly chicken, more particularly young poultry (at Day 3 post-hatch or earlier or in ovo), comprising administering to said non-human animal a composition, vaccine, DEV, nucleic acid or host cell as defined above.

A particular object of the invention is a method of vaccinating poultry comprising in ovo administration of a composition, vaccine, DEV, nucleic acid or host cell as defined above.

Another particular object of the invention is a method of vaccinating poultry comprising administration of a composition, vaccine, DEV, nucleic acid or host cell as defined above, at Day 1 or at Day 2 post-hatch.

In a further aspect, the invention provides a method for inducing an immunogenic or protective response in a non-human animal against one or more avian pathogens, comprising administering to said non-human animal, particularly poultry, more particularly chicken, more particularly young poultry (at Day 3 post-hatch or earlier) or in ovo, a composition, vaccine, DEV, nucleic acid or host cell as defined above.

As indicated in the experimental section, the viruses of the invention are particularly advantageous for vaccinating young poultry (at Day 1, Day 2 or Day 3 post-hatch) or for in ovo vaccination. Indeed, the invention surprisingly shows that the viruses of the invention are safe upon such early administration, while native or wild-type DEV is lethal. Such early administration, combined with the early onset of immunity caused by these viruses, are particularly advantageous to induce early protective immunity, before poultry can be substantially exposed to pathogens.

In this regard, in a more general aspect, the invention also relates to a method for vaccinating or immunizing an avian, particularly poultry, more particularly chicken, the method comprising in ovo administration to said avian of an attenuated DEV encoding an antigen. The invention also relates to a method for expressing a foreign gene in an avian, particularly poultry, more particularly chicken, the method comprising in ovo administration to said avian of an attenuated DEV containing said foreign gene. The invention also relates to the use of an attenuated DEV containing a foreign gene for expressing said gene into an avian by in ovo administration of said DEV. The invention also relates to an attenuated DEV encoding an antigen, for use to induce an immune response or to vaccinate an avian by in ovo administration of said DEV. The DEV preferably comprises an inactive endogenous gene, rendering said DEV attenuated and well tolerated upon in ovo injection.

The present invention further relates to vaccination kits for immunizing avian species which comprises an effective amount of the multivalent vaccine as described above and a means for administering said components to said species. For example, such kit comprises an injection device filled with the vaccine according to the invention and instructions for intradermic, subcutaneous, intramuscular, or in ovo injection.

Alternatively, the kit comprises a spray/aerosol or eye drop device filled with the vaccine according to the invention and instructions for oculo-nasal administration, oral or mucosal administration.

Further aspects and advantages of the invention will be disclosed in the following experimental section, which is illustrative of the claimed invention.

EXAMPLES

Example 1

Virulence of Wild-Type DEV in Eggs or Young Poultry

A clinical study was performed to investigate the pathogenicity or virulence of DEV in chicken upon injection at different time schedule. More particularly, injection was performed in ovo (Day 3 before hatch), at Day 1 post-hatch, or at Day 4 post-hatch. DEV used was a wild-type DEV Jansen strain. The administered dose was either 100 or 1000 pfu/dose. As a control a PBS solution was administered. Pathogenicity was assessed by measuring mortality each day after hatch.

The results are presented in the following table.

| Group | Vaccine | Dose pfu | Route | Day[1] | n | D 0 | D 1 | D 2 | D 3 | D 4 | D 5 | D 6 | D 7 | D 8 | >D 9[2] | % Mortality |
|---|---|---|---|---|---|---|---|---|---|---|---|---|---|---|---|---|
| 1 | PBS | — | in ovo | −3 | 17 | 0 | 0 | 0 | 0 | 0 | 0 | 0 | 0 | 0 | 2 | 12 |
| 2 | DEV | 100 | in ovo | −3 | 16 | 3 | 2 | 9 | 1 | 1 | — | — | — | — | — | 100 |
| 3 | DEV | 1000 | in ovo | −3 | 17 | 5 | 2 | 9 | 1 | — | — | — | — | — | — | 100 |
| 4 | DEV | 1000 | sc | 1 | 17 | 0 | 0 | 0 | 0 | 0 | 6 | 4 | 2 | 1 | 1 | 82 |
| 5 | DEV | 1000 | sc | 4 | 17 | 0 | 0 | 0 | 0 | 0 | 0 | 0 | 0 | 0 | 0 | 0 |

[1]Day of age at inoculation
[2]Number of birds died between 9-day to 19-days of age The above results show that injection of wtDEV at Day 4 post-hatch is safe with 100% survival rate (see group 5). In sharp contrast, after in ovo injection of DEV, 100% of birds died by 4-days of age, while in ovo injection of PBS is safe. These results thus show that, while wtDEV may be suitable for administration to adult animals, surprisingly, it is lethal in young animals (Day 3 or less post hatch) or when administered in ovo.

Example 2

Virulence of DEV Having an Inactive US4 or US5 Gene 2.1. Construction of DEV Comprising an Inactive US4 Gene or US5 Gene.

In an attempt to reduce the virulence to chick embryos, US4- or US5-inactive DEVs were constructed.

Construction of rpsLneo-DsRed2 Cassette

A 2.8-kb DNA fragment of rpsLneo-DsRed2 cassette was constructed by PCR reactions. Briefly, three PCR reactions were conducted. First PCR reaction was conducted using primer pair of SEQ ID NO: 1 (5'-GGCCTGGTGATGATG-GCGGGATCGTTGTAT-3') and SEQ ID NO: 2 (5'-CCATG-GTGCTGCGCTCAGAAGAACTCGTCA-3') with the template of synthesized fragment of rpsLneo (SEQ ID NO: 3). Second PCR reaction was conducted using primer pair of SEQ ID NO: 4 (5'-ACGAGTTCTTCTGAGCGCAGCAC-CATGGCC-3') and SEQ ID NO: 5 (5'-TCGGAGGAGGC-CATCCTTAAGAGCTGTAAT-3') with the template plasmid of pSI Mammalian Expression Vectors (Promega, Cat # E1721). Third PCR reaction was conducted using primer pair of SEQ ID NO: 6 (5'-TACAGCTCTTAAGGATGGC-CTCCTCCGAGA-3') and SEQ ID NO: 7 (5'-GCAGT-GAAAAAAATGCTTTATTTGTGAAAT-3') with the template plasmid of pIRES2-DsRed2 (Clontech, Cat #632420). Another PCR reaction was conducted using a mixture of PCR products from the first and second PCR reactions as a template and SEQ ID NO: 1 and SEQ ID NO: 5 as primers. This PCR product and the PCR product from third PCR reaction were mixed and used for final PCR reaction with primer pair of SEQ ID NO:1 and SEQ ID NO:7, resulting in rpsLneo-DsRed2 cassette.

Construction of Insertion Cassette

A DNA fragment of rpsLneo-DsRed2 cassette that was added DEV US4 or US5 region homologous sequences (50 bp each) of both 5' and 3' ends to both ends of it was constructed by PCR reaction. PCR reaction was conducted using rpsLneo-DsRed2 cassette as a template. Primer pair used is SEQ ID NO: 8 (5'-ATGGCAACAATGATAGCT-GTGGTGTTAGTTTTTTTGGGACGCGTTTTAGGGGC-CTGGTGATGATGGCGGG-3') and SEQ ID NO: 9 (5'-TTAAACTAATGGAACGCGTTGGAATTTCAAGTCTT GGCGCCCAAACATCGGCAGTGAAAAAAAT-GCTTTA-3') for US4-inactive DEV and SEQ ID NO: 10 (5'-ATGTATACAGACGTTACGGTCATGTGGGTAGC-CGTGATTTTATTTACTATGGCCTGGTGATGATG-GCGGG-3') and SEQ ID NO: 11 (5'-TCATACCATA-CAAAGGCATAGGTACAGCCCACAGGTTAAAAACA AAGAAAGCAGTGAAAAAAATGCTTTA-3') for US5-inactive DEV. Obtained PCR fragments (US4-rpsLneo-DsRed2 and US5-rpsLneo-DsRed2 cassettes) were electrophoresed and purified.

Construction of Recombinant DEV Carrying rpsLneo-DsRed2 Gene

Construction of recombinant DEV carrying rpsLneo-DsRed2 gene in US4 or US5 region was conducted by homologous recombination in *E. coli* strain carrying DEV genome, transfected with 0.5 μg of either US4-rpsLneoD-sRed2 or US5-rpsLneoDsRed2. Transfection was conducted by electroporation using Gene Pulser Xcell (Bio-Rad Laboratories) at 1.75 kV, 25 μF, and 200 ohm. After transfection, the *E. coli* was planted onto Luria-Bertani (LB) agar plates, and incubated overnight at 30° C. *E. coli* clones carrying an appropriate insert containing the rpsLneo-DsRed2 gene in US4 or US5 regions were identified by PCR using primer pair amplifying a region between rpsLneo-DsRed2 gene and the insertion site region of DEV genome (Junction 1). The primers are SEQ ID NO: 12 (5'-AAGTGTATAAATTAGA-CAAGTAGCTATGCG-3') and SEQ ID NO: 13 (5'-TCA-GAAGAACTCGTCAAGAAGGC-3') for US4-inactive DEV and SEQ ID NO: 13 and SEQ ID NO: 14 (5'-GTTTATATTGACGCGGAATGTTGAC-3') for US5-inactive DEV. DEV DNA was extracted from *E. coli* clones carrying an appropriate insert and transfected into CEF using Nucleofector II (Lonza, Basel, Switzerland). The transfected cells were added to Leibovitz's L-15 (Life Technologies Corp., Cat. #41300-39), McCoy's 5A Medium (Life Technologies Corp., Cat. #21500-061) (1:1) and 4% calf serum [LM (+) medium], planted in 96-well tissue culture plates, and then incubated at 37° C. in 4-5% $CO_2$ for 5-7 days until DEV cytopathic effect (CPE) became visible. DEVs carrying rpsLneo-DsRed2 gene in US4 or US5 regions were successfully rescued (DEV/US4/rpsLneo-DsRed2 or DEV/US5/rpsLneo-DsRed2).

Verification of Genome Structure

Genome structure of the recombinant DEV/US4/rpsLneo-DsRed2 or DEV/US5/rpsLneo-DsRed2 was verified by three PCR reactions amplifying junction regions (Junction 1, Junction 2, and Junction 3) at each end of the inserted gene. The primer pairs used in the PCR reactions for Junction 1 are described above. In DEV/US4/rpsLneo-DsRed2, the primers pair used in the PCR reactions are SEQ ID NO: 6 and SEQ ID NO: 15 (5'-CATTTTAACCGTTTAAGTCAACAT-TCCGC-3') for Junction 2 and SEQ ID NO: 12 and SEQ ID NO: 15 for Junction 3. In DEV/US5/rpsLneo-DsRed2, the primer pairs used in the PCR reactions is SEQ ID NO: 6 and SEQ ID NO: 16 (5'-ACTGAGATGTTGGACCAT-CAAATCCTG-3') for Junction 2 and SEQ ID NO: 14 and SEQ ID NO: 16 for Junction 3. Expected sizes of PCR products were observed, confirming that DEV/US4/rpsLneo-DsRed2 and DEV/US5/rpsLneo-DsRed2 had the expected genome structures.

2.2. Expression of Foreign Gene by Recombinant DEVs having an Inactive US4 or US5 Gene.

Expression of the DsRed2 protein by DEV/US4/rpsLneo-DsRed2 or DEV/US5/rpsLneo-DsRed2 was confirmed by excitation for DsRed2. Excitation for DsRed2 was conducted using CEF infected with DEV/US4/rpsLneo-DsRed2 or DEV/US5/rpsLneo-DsRed2. Briefly, CEF cells in 6-well plate were infected with DEV/US4/rpsLneo-DsRed2, DEV/US5/rpsLneo-DsRed2, or the parent DEV strain at a multiplicity of infection of approximately 0.01. Three days post inoculation, cells were excited at 563 nm and red fluorescence was observed in the plaques of recombinant DEV/US4/rpsLneo-DsRed2 or DEV/US5/rpsLneo-DsRed2, thus confirming actual protein expression by the recombinant DEVs.

2.3. Viability and Stability of Recombinant DEVs having an Inactive US4 or US5 Gene.

DEV/US4/rpsLneo-DsRed2 or DEV/US5/rpsLneo-DsRed2 were passaged in CEF at fifteen times and confirmed stability of inserted gene of rpsLneo-DsRed2. Passage was conducted every three to four days. Every five passages, plaques of DEV/US4/rpsLneo-DsRed2 or DEV/US5/rpsLneo-DsRed2 were checked red fluorescence by fluorescence microscope and genome structures of them were confirmed by PCR analysis amplifying junction regions (Junction 1, Junction 2, and Junction 3) with the primers shown in Example 2. Red fluorescence and expected sizes of PCR products were observed all of the observed viruses, confirming that DEV/US4/rpsLneo-DsRed2 and DEV/US5/rpsLneo-DsRed2 retained rpsLneo-DsRed2 gene for at least fifteen passages.

2.4. Virulence of US4 or US5 Inactive DEV upon In Ovo Administration.

DEV/US4/rpsLneo-DsRed2 or DEV/US5/rpsLneo-DsRed2 were inoculated into 18-days-old embryo of SPF chickens to investigate their pathogenicity or virulence to chick embryos. Chick embryos were administered in ovo with approximately 1000 pfu/0.1 ml of DEV/US4/rpsLneo-DsRed2, DEV/US5/rpsLneo-DsRed2, parental DEV, or 0.1 ml of PBS via 20 gauge and 1.5 inch needles. Chicks were observed daily for clinical signs associated with DEV, such as depression and death for 11 days. The results are shown in the following table.

| Vaccine | n | Not hatch | D 0 | D 1 | D 2 | D 3 | D 4 | D 5 | >D 6[1] | % Mortality |
|---|---|---|---|---|---|---|---|---|---|---|
| PBS | 22 | 2 | 0 | 0 | 0 | 0 | 2 | 0 | 0 | 18 |
| DEV/US4/rpsLneo-DsRed2 | 22 | 5 | 3 | 1 | 6 | 5 | 2 | — | — | 100 |
| DEV/US5/rpsLneo-DsRed2 | 22 | 2 | 6 | 0 | 6 | 4 | 4 | — | — | 100 |
| DEV | 22 | 0 | 6 | 1 | 8 | 4 | 2 | 0 | 0 | 95 |

[1]Number of birds died between 6-day to 11-days of age

All chicks inoculated in ovo with US4- or US5-inactive DEVs died 4 days after hatch, while 95% of the chicks inoculated with parental DEV died. This results show that US4- or US5-inactive DEV still have pathogenicity and virulence to chick embryos upon in ovo administration.

Example 3

Construction of DEVs Comprising Inactive US4 and US5 Genes

For construction of US4 and US5 inactive DEV, a homology vector was first constructed and then used to generate the virus by homologous recombination in *E. coli*. Plasmid constructions and DNA manipulation were essentially performed according to standard molecular biology techniques (Molecular Cloning: A Laboratory Manual. 4th Edition, Cold Spring Harbor Laboratory, Cold Spring Harbor, N.Y., USA, 2012).

Construction of the Homology Vector

A 1.1-kb DNA fragment of DEV genome flanking the US3 and US6 genes was cloned by PCR reactions adding SfiI recognition site at the insertion site. Briefly, using DNA extracted from DEV as a template, two PCR reactions were conducted. Primer pairs used are SEQ ID NO: 17 (5'-GCGCATGCTAGCTGATCTAACTTTAC-3') and SEQ ID NO: 18 (5'-GGTGGCCAATAAGGCCTGACG-GCAATATGT-3'), and SEQ ID NO: 19 (5'-TCAggccttattg-gccACCAGCTACACAAG-3') and SEQ ID NO: 20 (5'-GCGAATTCGATTAATTCTCCCGAACTGTTG-3').

Figure 2:
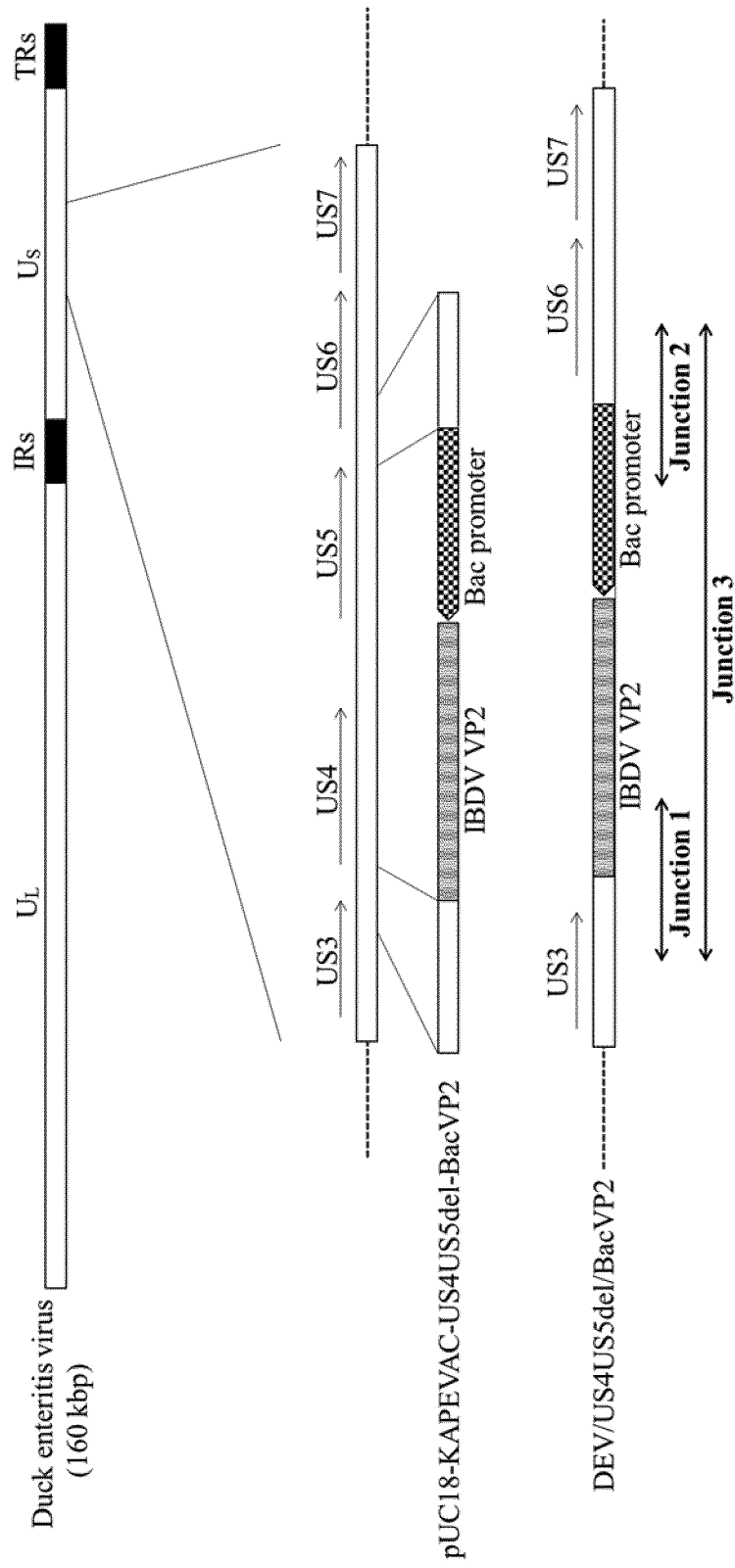
FIG. 2 illustrates schematic diagrams of the location of the insertion site in parental DEV genome and the genome structures of pUC18-KAPEVAC-US4US5del-BacVP2 and DEV/US4US5del/BacVP2. The locations of Junction 1, Junction 2, and Junction 3 used for amplification in PCR reactions are shown.

Another PCR reaction was conducted using a mixture of PCR products from the two previous PCR reactions as templates and SEQ ID NO: 17 and SEQ ID NO: 20 as primers. An obtained PCR fragment was cloned into pUC18 vector (GenBank Acc. No. L09136) after digestion with EcoRI and SphI, resulting in pUC18-KAPEVAC-US4US5del-SfiI, Which comprises a part of US3 and US6 region of DEV genome. Next, a homology vector containing a promoter and IBDV VP2 gene from standard challenge strain (VP2-STC) was constructed by utilizing plasmid pUC18-KAPEVAC-US4US5del-SfiI. First, pUC18-KAPE-VAC-US4US5del-SfI was cleaved with SfiI and dephosphorylated with Alkaline Phosphatase *Shewanella* sp. S1B1 Recombinant (PAP) (Funakoshi # DE110). Then, chicken Beta-actin (Bac) promoter (SEQ ID NO: 21) and VP2-STC genes were obtained by BglI digestion of p45/46bacVP2-STC #11 (U.S. Pat. No. 6,764,684). Finally, this Bac promoter-VP2-STC cassette was inserted into the SfiI-digested pUC18-KAPEVAC-US4US5del-SfiI, resulting in pUC18-KAPEVAC-US4US5del-BacVP2stc (FIG. 2). This plasmid, pUC18-KAPEVAC-US4US5del-BacVP2stc, was used to construct DEV/US4US5del/BacVP2stc (FIG. 2).

Construction of DEV/US4US5del/BacVP2

Construction of DEV carrying BacVP2 gene in US4-US5 region was conducted by homologous recombination in *E. coli* strain carrying DEV genome, transfected with 0.5 μg of pUC18-KAPEVAC-US4US5del-BacVP2stc. Transfection condition was described in Example 2. *E. coli* clones carrying an appropriate insert containing the BacVP2 gene were identified by PCR using primer pair amplifying a region between BacVP2 gene and the insertion site region of DEV genome (Junction 1, FIG. 2). The primers are SEQ ID NO: 22 (5'-GTCCACTATGCCATGACATAGGTG-3') and SEQ ID NO: 23 (5'-GAGCAACTTCGAGCTGATCC-3'). DEV DNA was extracted from *E. coli* clones carrying an appropriate insert and transfected into CEF. The transfected cells were incubated until DEV CPE became visible. DEV/US4US5del/BacVP2, which is knocked out its US4 and US5 genes and has BacVP2 gene, was successfully constructed.

Verification of Genome Structure

Genome structure of DEV/US4US5del/BacVP2 was verified by three PCR reactions amplifying junction regions (Junction 1, Junction 2, and Junction 3; FIG. 2) at each end of the inserted gene. The primer pairs used in the PCR reactions for Junction 1 are described above. The primer pair used in the PCR reactions for Junction 2 is SEQ ID NO: 24 (5'-GCCAGGGAATCCAGGGAAAAAGAC-3') and SEQ ID NO: 12. For Junction 3, SEQ ID NO: 22 and SEQ ID NO: 12 were used. Expected sizes of PCR products were observed, confirming that DEV/US4US5del/BacVP2 had the expected genome structure.

Example 4

Expression of VP2 Gene by DEV/US4US5del/BacVP2

Expression of the VP2 protein by the recombinant DEV/US4US5del/BacVP2 was confirmed by black plaque assay. In brief, CEF infected with DEV/US4US5del/BacVP2s were fixed with methanol:acetone mixture (1:2) and incubated with anti-IBDV VP2 monoclonal antibody R63 (ATCC #: HB-9490). Next, incubated with biotinylated anti-mouse IgG antibody (Vector Laboratories, Cat #

Figure 3:
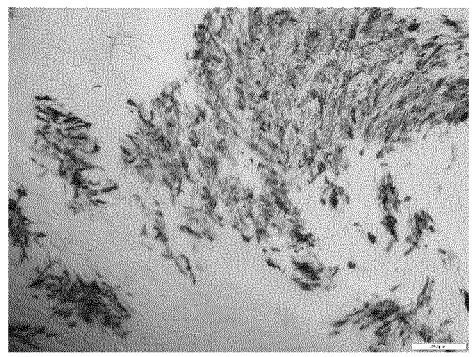
FIG. 3 shows VP2 expression by CEF infected with DEV/US4US5del/BacVP2 in black plaque assay.
Figure 4:
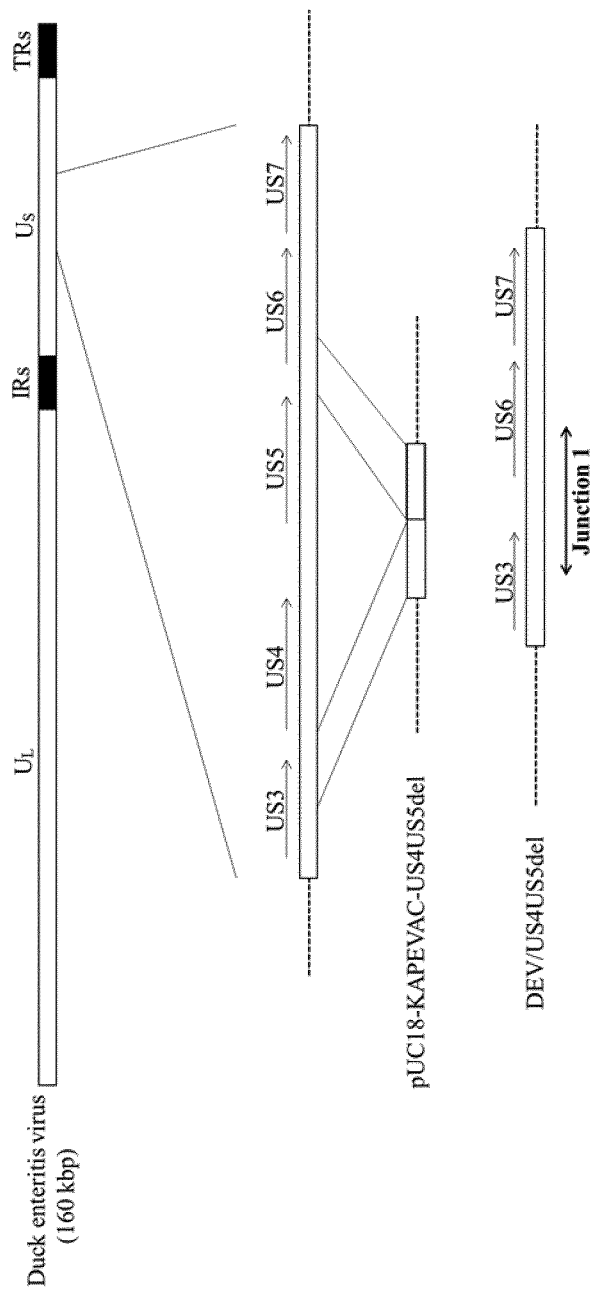
FIG. 4 illustrates schematic diagrams of the location of the insertion site in parental DEV genome and the genome structures of pUC18-KAPEVAC-US4US5del and DEV/US4US5del. The locations of Junction 1 used for amplification in PCR reaction is shown.
Figure 5:
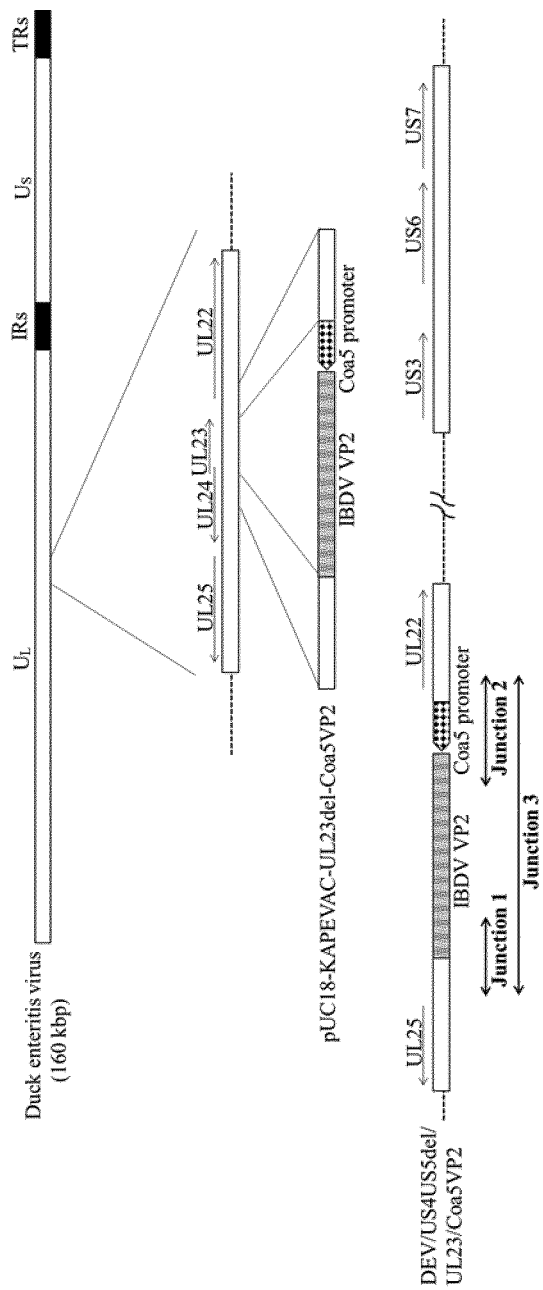
FIG. 5 illustrates schematic diagrams of the location of the insertion site in parental DEV genome and the genome structures of pUC18-KAPEVAC-UL23del-Coa5VP2 and DEV/US4US5del/UL23/Coa5VP2. The locations of Junction 1, Junction 2, and Junction 3 used for amplification in PCR reactions are shown.
Figure 6:
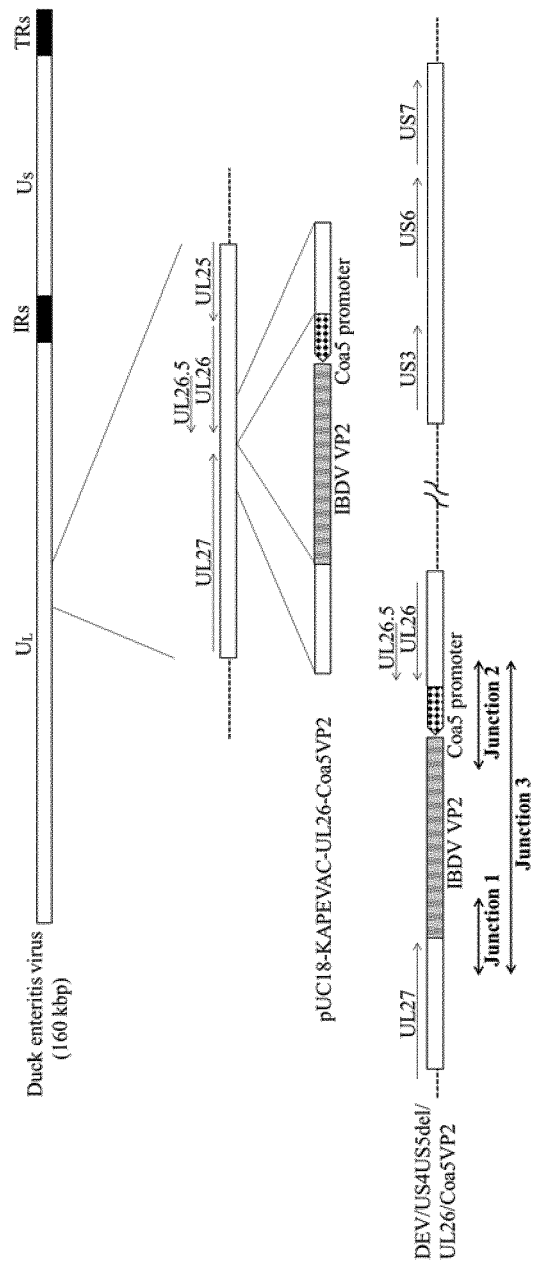
FIG. 6 illustrates schematic diagrams of the location of the insertion site in parental DEV genome and the genome structures of pUC18-KAPEVAC-UL26-Coa5VP2 and DEV/US4US5del/UL26/Coa5VP2. The locations of Junction 1, Junction 2, and Junction 3 used for amplification in PCR reactions are shown.

BA-9200) and then with VECTASTAIN ABC-AP kit (Vector Laboratories, Cat # AK-5000), plaques expressing VP2 protein were stained by addition of NBT/BCIP solution (Roche Applied Science, Cat #1681451). As shown in FIG. 3, expression of the VP2 protein was observed in the cells infected with DEV/US4US5del/BacVP2.

Example 5

In Ovo Administration of DEV/US4US5del/BacVP2

DEV/US4US5del/BacVP2 were inoculated into 18-days-old embryo of SPF chicks. All groups of embryos were vaccinated in ovo with approximately 1000 pfu/0.1 ml of the recombinant DEV/US4US5del/BacVP2, parental DEV, or 0.1 ml of PBS via 20 gauge and 1.5 inch needles. Chicks were observed daily for clinical signs associated with DEV, such as depression and death, for 35 days. Five weeks post hatch, chickens were examined for weight gain and necropsied and observed for grossly observable lesions. The results are shown in the following table.

| | | not | Number of birds to death in each day of age | | | | | | | | % | Depressed | Average |
|---|---|---|---|---|---|---|---|---|---|---|---|---|---|
| vaccine | n | hatch | D 0 | D 1 | D 2 | D 3-D 8[1] | D 9 | D 10 | D 11 | >D 12[2] | mortality | birds | of BW(g) |
| PBS | 16 | 0 | 0 | 0 | 0 | 0 | 0 | 0 | 0 | 0 | 0.0 | 0 | 433.3 |
| DEV/US4US5del/BacVP2 | 17 | 0 | 0 | 0 | 0 | 0 | 1 | 0 | 1 | 0 | 11.8 | 0 | 468.3 |
| DEV | 17 | 7 | 4 | 0 | 6 | — | — | — | — | — | 100.0 | — | — |

[1]Number of birds died between 3-day to 8-days of age

[2]Number of birds died between 12-day to 35-days of age

Mortality of the birds inoculated with DEV/US4US5del/BacVP2, which was knocked out for both US4 and US5 genes, was 11.8%, whereas that with parental DEV was 100%, showing that virulence and pathogenicity of DEV were substantially reduced by inactivation (e.g. deletion) of both US4 and US5 genes. In addition, average body weight of the survived birds inoculated with DEV/US4US5del/BacVP2 was comparable to that with PBS. These results allow to demonstrate the efficacy of the DEVs of the invention for in ovo vaccination.

Example 6

Construction of DEV/Coa5VP2 Comprising Inactive US4 and US5 Genes

In this section, DEVs which had deletion in both US4 and US5 genes and carried VP2 gene driven by core region of Bac promoter (Coa5 promoter; SEQ ID NO: 25) were constructed. For construction of these DEVs, homology vectors were first constructed and then used to generate the viruses by homologous recombination in *E. coli.*

Construction of pUC18-KAPEVAC-US4US5del

A 1.1-kb DNA fragment of DEV genome flanking the US3 and US6 genes was cloned by PCR reactions (FIG. 4). Briefly, using DNA extracted from DEV as a template, two PCR reactions were conducted. Primer pairs used are SEQ ID NO: 17 and SEQ ID NO: 26 (5'-GCTTGTGTAGCTGGTTGACGGCAATATG-3'), and SEQ ID NO: 27 (5'-CATATTGCCGTCAACCAGCTACACAAGC-3') and SEQ ID NO: 20 (5'-gcGAATTCGATTAATTCTCCCGAACTGTTG-3'). Another PCR reaction was conducted using a mixture of PCR products from the two previous PCR reactions as a template and SEQ ID NO: 17 and SEQ ID NO: 20 as primers. An obtained PCR fragment was cloned into pUC18 vector after digestion with EcoRI and SphI, resulting in pUC18-KAPEVAC-US4US5del (FIG. 4).

Construction of DEV/US4US5del

Construction of recombinant DEV/US4US5del which has deletion in both US4 and US5 genes was conducted by homologous recombination in *E. coli* carrying a DEV genome, transfected with 0.5 μg of pUC18-KAPEVAC-US4US5del. *E. coli* clones carrying an appropriate deletion (DH10B/DEV/US4US5del) were identified by PCR using primer pair amplifying a region between US3 and US6 (Junction 1; FIG. 4). The primers used are SEQ ID NO: 22 and SEQ ID NO: 20. DEV DNA was extracted from *E. coli* clones and transfected into CEF to rescue DEV/US4US5del.

Construction of pUC18-KAPEVAC-UL23del-Coa5VP2

A 1.0-kb DNA fragment of DEV genome flanking the UL24 and UL22 genes was cloned by PCR reactions adding SfiI recognition site at the insertion site (FIG. 5). Briefly, using DNA extracted from DEV as a template, two PCR reactions were conducted. Primer pairs used are SEQ ID NO: 28 (5'-GCGCATGCCAATTGTCTAATTCCAG-3') and SEQ NO: 29 (5'-CCCGGCCAATAAGGCCACAGAAAAAGCGCG-3'), and SEQ ID NO: 30 (5'-CTGTGGCCTTATTGGCCGGGATCTGGAAC-3') and SEQ ID NO: 31 (5'-GCGAATTCATGTGCTACGCCCAG-3'). Another PCR reaction was conducted using a mixture of PCR products from the two previous PCR reactions as a template and SEQ ID NO: 28 and SEQ ID NO: 31 as primers. An obtained PCR fragment was cloned into pUC18 vector after digestion with EcoRI and SphI, resulting in pUC18-KAPEVAC-UL23del-SfiI. Next, a homology vector containing a promoter and VP2-STC was constructed by utilizing plasmid pUC18-KAPEVAC-UL23del-SfiI. First, pUC18-KAPEVAC-UL23del-SfiI was cleaved with SfiI and dephosphorylated with PAP. The Coa5 promoter was obtained from the plasmid pGICOA (U.S. Pat. No. 6,866,852) by BglI and XbaI digestion, and ligated with a XbaI-EcoRI fragment (6.3-kb) and an EcoRI-BglI fragment (0.1-kb) of p45/46bacVP2-STC #11 (U.S. Pat. No. 6,764,684), resulting in p45/46COA5VP2-STC #11. The Coa5 promoter-VP2-STC cassette was then cut out from p45/46COA5VP2-STC #11 by BglI digestion and ligated with the SfiI-digested pUC18-KAPEVAC-UL23del-SfiI, resulting in pUC18-KAPEVAC-UL23del-Coa5VP2. This plasmid was used to construct DEV/US4US5del/UL23/Coa5VP2.

Construction of pUC18-KAPEVAC-UL26-Coa5VP2

A 1.0-kb DNA fragment of DEV genome flanking the UL26 and UL27 genes was cloned by PCR reactions adding SfiI recognition site at the insertion site (FIG. 6). Briefly, using DNA extracted from DEV as a template, two PCR reactions were conducted. Primer pairs used are SEQ ID NO: 32 (5'-CGGTCGACACTCCCAGGGGTGAAGC-3') and SEQ ID NO: 33 (5'-CGGCCAATAAGGCCAAGAAT-GCATTCGGCC-3'), and SEQ ID NO: 34 (5'-TGGCCTT-ATTGGCCGCCGTATGAATTGCGC-3') and SEQ ID NO: 35 (5'-GCGAGCTCCTGCAACCACAGACCGC-3'). Another PCR reaction was conducted using a mixture of PCR products from the two previous PCR reactions as a template and SEQ ID NO: 32 and SEQ ID NO: 35 as primers. An obtained PCR fragment was cloned into pUC18 vector after digestion with SalI and SacI, resulting in pUC18-KAPEVAC-UL26-SfiI. Next, a homology vector containing a promoter and IBDV VP2 gene from standard challenge strain was constructed by utilizing plasmid pUC18-KAPEVAC-UL26-SfiI. First, pUC18-KAPEVAC-UL26-SfiI was cleaved with SfiI and dephosphorylated with PAP. The Coa5 promoter-VP2-STC cassette was cut out from pUC18-KAPEVAC-UL23del-Coa5VP2 by SfiI digestion and ligated with the SfiI-digested pUC18-KAPEVAC-UL26-SfiI, resulting in pUC18-KAPEVAC-UL26-Coa5VP2. This plasmid was used to construct DEV/US4US5del/UL26/Coa5VP2.

Construction of pUC18-KAPEVAC-UL45-Coa5VP2

Figure 7:
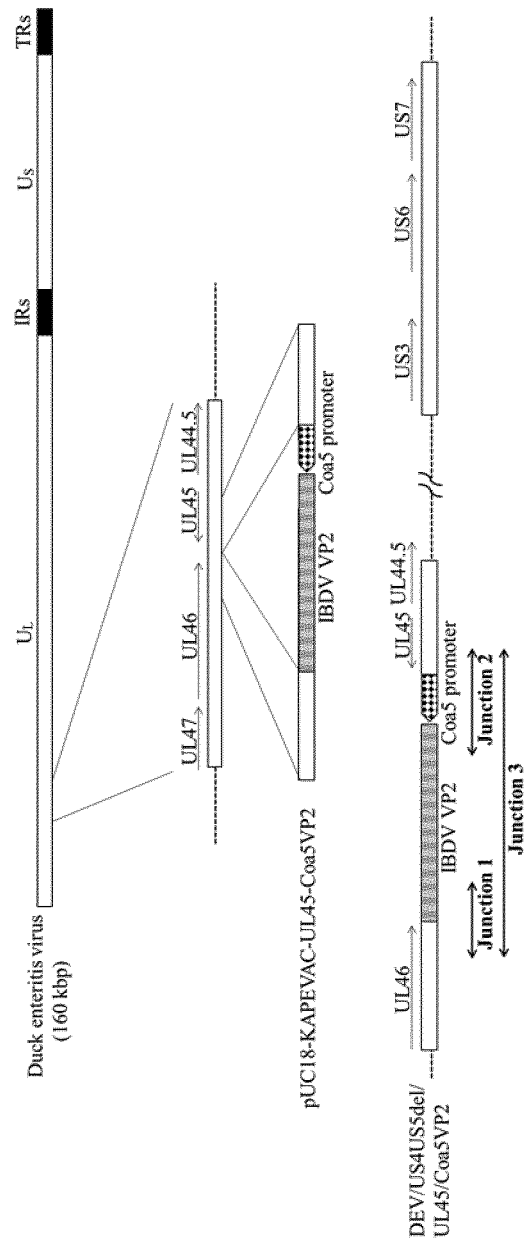
FIG. 7 illustrates schematic diagrams of the location of the insertion site in parental DEV genome and the genome structures of pUC18-KAPEVAC-UL45-Coa5VP2 and DEV/US4US5del/UL45/Coa5VP2. The locations of Junction 1, Junction 2, and Junction 3 used for amplification in PCR reactions are shown.

A 1.0-kb DNA fragment of DEV genome flanking the UL45 and UL46 genes was cloned by PCR reactions adding SfiI recognition site at the insertion site (FIG. 7). Briefly, using DNA extracted from DEV as a template, two PCR reactions were conducted. Primer pairs used are SEQ ID NO: 36 (5'-CGGTCGACATAGAACGCGCTTCATCTAA-3') and SEQ ID NO: 37 (5'-TGGCCAATAAGGCCGTTT-ATTGTTTATTAT-3'), and SEQ ID NO: 38 (5'-CGGCCTT-ATTGGCCAATCTGATTCATCCAA-3') and SEQ ID NO: 39 (5'-GCGAGCTCCGCCTAATCACAATCGGTATTG-3'). Another PCR reaction was conducted using a mixture of PCR products from the two previous PCR reactions as a template and SEQ ID NO: 36 and SEQ ID NO: 39 as primers. An obtained PCR fragment was cloned into pUC18 vector after digestion with SalI and SacI, resulting in pUC18-KAPEVAC-UL45-SfiI. Next, a homology vector containing a promoter and IBDV VP2 gene from standard challenge strain was constructed by utilizing plasmid pUC18-KAPEVAC-UL45-SfiI. First, pUC18-KAPEVAC-UL45-SfiI was cleaved with SfiI and dephosphorylated with PAP. The Coa5 promoter-VP2-STC cassette was cut out from pUC18-KAPEVAC-UL23del-Coa5VP2 by SfiI digestion and ligated with the SfiI-digested pUC18-KAPEVAC-UL45-SfiI, resulting in pUC18-KAPEVAC-UL45-Coa5VP2. This plasmid was used to construct DEV/US4US5del/UL45/Coa5VP2.

Construction of pUC18-KAPEVAC-UL50-Coa5VP2

Figure 8:
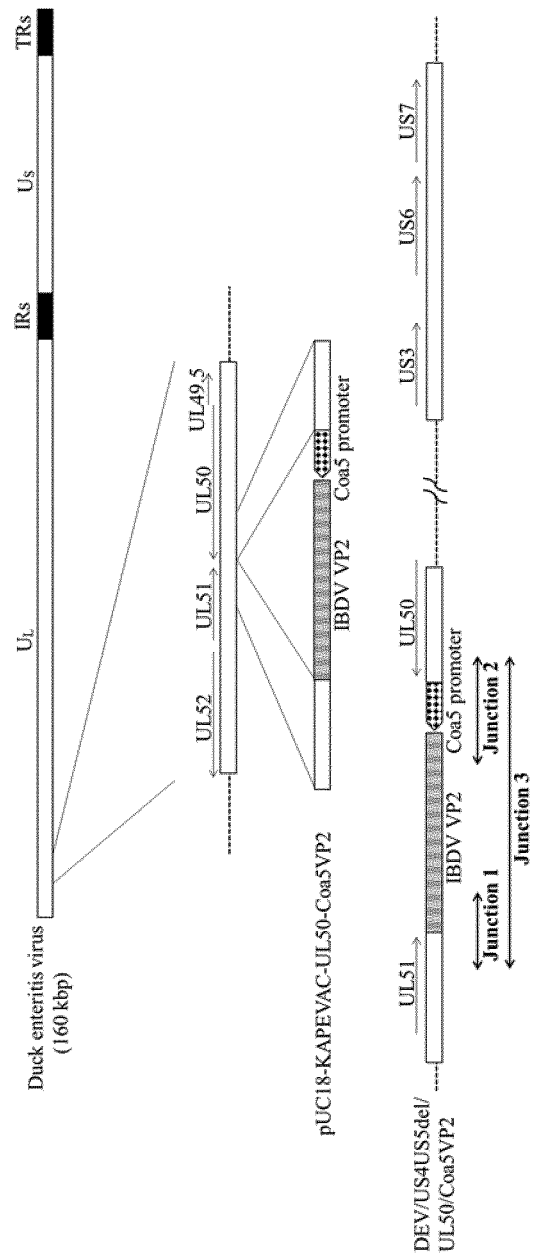
FIG. 8 illustrates schematic diagrams of the location of the insertion site in parental DEV genome and the genome structures of pUC18-KAPEVAC-UL50-Coa5VP2 and DEV/US4US5del/UL50/Coa5VP2. The locations of Junction 1, Junction 2, and Junction 3 used for amplification in PCR reactions are shown.

A 1.0-kb DNA fragment of DEV genome flanking the UL50 and UL51 genes was cloned by PCR reactions adding SfiI recognition site at the insertion site (FIG. 8). Briefly, using DNA extracted from DEV as a template, two PCR reactions were conducted. Primer pairs used are SEQ ID NO: 40 (5'-CCGCATGCGCAACTATATATGTCGGTC-3') and SEQ ID NO: 41 (5'-GGGCCAATAAGGCCCAAAAG-TACATTTGT-3'), and SEQ ID NO: 42 (5'-GGGCCTTAT-TGGCCCAATTTATTTACTATT-3') and SEQ ID NO: 43 (5'-GCGAATTCTGGATATGATATACCGTTGC-3'). Another PCR reaction was conducted using a mixture of PCR products from the two previous PCR reactions as a template and SEQ ID NO: 40 and SEQ ID NO: 43 as primers. An obtained PCR fragment was cloned into pUC18 vector after digestion with EcoRI and SphI, resulting in pUC18-KAPEVAC-UL50-SfiI. Next, a homology vector containing a promoter and IBDV VP2 gene from standard challenge strain was constructed by utilizing plasmid pUC18-KAPEVAC-UL50-SfiI. First, pUC18-KAPEVAC-UL50-SfiI was cleaved with SfiI and dephosphorylated with PAP. The Coa5 promoter-VP2-STC cassette was cut out from pUC18-KAPEVAC-UL23del-Coa5VP2 by SfiI digestion and ligated with the SfiI-digested pUC18-KAPEVAC-UL50-SfiI, resulting in pUC18-KAPEVAC-UL50-Coa5VP2. This plasmid was used to construct DEV/US4US5del/UL50/Coa5VP2.

Construction of DEV/US4US5del/Coa5VP2stc

Construction of recombinant DEVs which have deletion in US4 and US5 genes and carry Coa5VP2 gene in UL23, UL26/UL27, UL45/UL46, or UL50/UL51 regions was conducted by homologous recombination in E. coli strain transfected with DEV/US4US5del and with 0.5 µg of one of pUC18-KAPEVAC-UL23del-Coa5VP2, pUC18-KAPE-VAC-UL26-Coa5VP2, pUC18-KAPEVAC-UL45-Coa5VP2, or pUC18-KAPEVAC-UL50-Coa5VP2. Transfection condition was described in Example 2. After transfection, E. coli clones carrying an appropriate insert containing the Coa5VP2 gene were identified by PCR using primer pair amplifying a region between Coa5VP2 gene and the insertion site region of DEV genome (Junction 1, FIG. 5-8). The primers are SEQ ID NO: 23 and SEQ ID NO: 28 for insertion site UL23, SEQ ID NO: 32 for insertion site UL26/UL27, SEQ ID NO: 36 for insertion site UL45/UL46, or SEQ ID NO: 40 for insertion site UL50/UL51. Modified DEV DNAs were extracted from E. coli clones carrying an appropriate insert and transfected into CEF using Nucleofector II. The transfected cells were added to LM (+) medium, planted in 96-well tissue culture plates, and then incubated at 37° C. in 4-5% $CO_2$ for 5-7 days until DEV CPE became visible. After transfection, DEVs which have inactive US4 and US5 genes and carry Coa5VP2 gene were successfully rescued (DEV/US4US5del/UL23/Coa5VP2, DEV/US4US5del/UL26/Coa5VP2, DEV/US4US5del/UL45/Coa5VP2, and DEV/US4US5del/UL50/Coa5VP2).

Verification of Genome Structure

Genome structures of DEV/US4US5del/UL23/Coa5VP2, DEV/US4US5del/UL26/Coa5VP2, DEV/US4US5del/UL45/Coa5VP2, and DEV/US4US5del/UL50/Coa5VP2 were verified by three PCR reactions amplifying junction regions (Junction 1, Junction 2, and Junction 3; FIG. 5-8) at each end of the inserted gene. The primer pairs used in the PCR reactions for Junction 1 are described above. The primer pair used in the PCR reactions for Junction 2 is SEQ ID NO: 24 and SEQ ID NO: 31 (insertion site UL23), SEQ ID NO: 35 (insertion site UL26/UL27), SEQ ID NO: 39 (insertion site UL45/UL46), or SEQ ID NO: 43 (insertion site UL50/UL51). For Junction 3, primer pairs SEQ ID NO: 28/SEQ ID NO: 31 (insertion site UL23), SEQ ID NO: 32/SEQ ID NO: 32/SEQ ID NO: 35 (insertion site UL26/UL27), SEQ ID NO: 36/SEQ ID NO: 39 (insertion site UL45/UL46), or SEQ ID NO: 40/SEQ ID NO: 43 (insertion site UL50/UL51) were used. Expected sizes of PCR products were observed, confirming that DEV/US4US5del/UL23/Coa5VP2, DEV/US4US5del/UL26/Coa5VP2, DEV/US4US5del/UL45/Coa5VP2, and DEV/US4US5del/UL50/Coa5VP2 had the expected genome structure.

Example 7

Expression of VP2 Gene by DEV/Coa5VP2 Comprising Inactive US4 and US5 Genes

Expression of the VP2 protein by DEV/US4US5del/UL23/Coa5VP2, DEV/US4US5del/UL26/Coa5VP2, DEV/US4US5del/UL45/Coa5VP2, and DEV/US4US5del/UL50/

Figure 9:
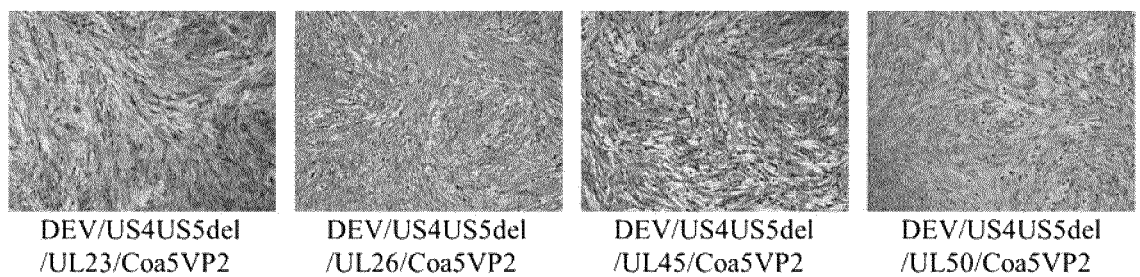
FIG. 9 shows VP2 expression by CEF infected with DEV/US4US5del/UL23/Coa5VP2, DEV/US4US5del/UL26/Coa5VP2, DEV/US4US5del/UL45/Coa5VP2, or DEV/US4US5del/UL50/Coa5VP2 in black plaque assay.
Figure 10:
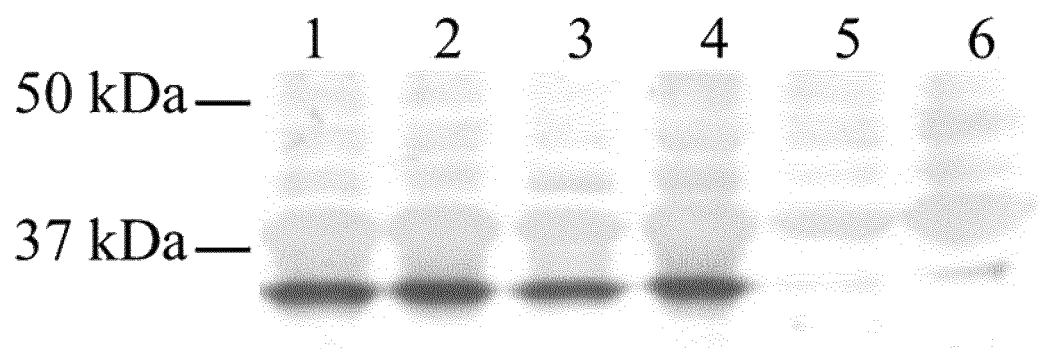
FIG. 10 is a western blot assay detecting expression of VP2 protein by DEV/US4US5del/UL23/Coa5VP2, DEV/US4US5del/UL26/Coa5VP2, DEV/US4US5del/UL45/Coa5VP2, or DEV/US4US5del/UL50/Coa5VP2. 1: DEV/US4US5del/UL23/Coa5VP2; 2: DEV/US4US5del/UL26/Coa5VP2; 3: DEV/US4US5del/UL45/Coa5VP2; 4: DEV/US4US5del/UL50/Coa5VP2; 5: Parental DEV; 6: CEF.

Coa5VP2 was confirmed by black plaque assay and western blot analysis. The method of black plaque assay was described in Example 4. As shown in FIG. 9, expression of the VP2 protein was observed in the cells infected with DEV/US4US5del/UL23/Coa5VP2, DEV/US4US5del/UL26/Coa5VP2, DEV/US4US5del/UL45/Coa5VP2, or DEV/US4US5del/UL50/Coa5VP2. The western blot was conducted using CEF infected with DEV/US4US5del/UL23/Coa5VP2, DEV/US4US5del/UL26/Coa5VP2, DEV/US4US5del/UL45/Coa5VP2, or DEV/US4US5del/UL50/Coa5VP2 and anti-IBDV VP2 monoclonal antibody R63. Briefly, CEF in 12-well plates was infected with one of the recombinant viruses or parental DEV. Four days post inoculation, cells were harvested with trypsin and centrifuged at 913×g for 5 minutes. The pellet was washed with PBS and resuspended with 25 µl of PBS. After adding the same volume of 2×SDS sample buffer (130 mM Tris-Cl (pH6.8), 6% SDS, 20% Glycerol, 10% 2-Mercaptoethanol and 0.01% Bromo Phenol Blue), cell suspension was boiled for 5 minutes. The samples were separated by SDS-PAGE using 12.5% polyacrylamide gel and transferred to a PVDF membrane (Immobilon-P, Millipore). The membrane was dried completely and then incubated with the R63 monoclonal antibody. After the R63 antibody was washed off, biotinylated anti-mouse IgG antibody and then with VECTASTAIN ABC-AP kit. Protein bound with the R63 monoclonal antibody was visualized by addition of NBT/BCIP solution. Protein bands of 40 kilodaltons, which is the expected size of VP2 protein, were observed in all lanes with the recombinant cells (FIG. 10), confirming that cells infected with recombinant viruses expressed VP2 protein.

Example 9

Stability of DEV/Coa5VP2 Comprising Inactive US4 and US5 Genes

DEV/US4US5del/UL23/Coa5VP2, DEV/US4US5del/UL26/Coa5VP2, DEV/US4US5del/UL45/Coa5VP2, and DEV/US4US5del/UL50/Coa5VP2 were passaged in CEF at fifteen times and stability of inserted gene of BacVP2 was duly confirmed. Passage was conducted every three to four days. Every five passages, cells infected with DEV/US4US5del/UL23/Coa5VP2, DEV/US4US5del/UL26/Coa5VP2, DEV/US4US5del/UL45/Coa5VP2, or DEV/US4US5del/UL50/Coa5VP2 were checked for the expression of VP2 gene by black plaque assay and their genome structures were confirmed by PCR analysis amplifying junction regions (Junction 1, Junction 2, and Junction 3; FIG. 5-8) with the primers shown in Example 7. As a result, no reversion of the US4 and US5 gene and no deletion on Coa5VP2 gene were observed, showing that these viruses are stable in CEF.

Example 10

In Ovo Administration of DEV/Coa5VP2 Comprising Inactive US4 and US5 Genes

In this study, in ovo safety and protective efficacy against virulent IBDV are examined.

DEV/US4US5del/UL23/Coa5VP2, DEV/US4US5del/UL26/Coa5VP2, DEV/US4US5del/UL45/Coa5VP2, and DEV/US4US5del/UL50/Coa5VP2, or parental DEV, are inoculated into 18-days-old embryo of SPF chickens. All groups of embryos are vaccinated in ovo with approximately 1000 pfu/0.1 ml of the recombinant viruses, parental DEV, or 0.1 ml of PBS via 20 gauge and 1.5 inch needles. Chicks are observed daily for clinical signs associated with DEV, such as depression and death, for 42 days. They are bled and examined for weight each week between 1 and 5 weeks of age for evaluation of humoral immunity against IBDV and for check the virulence of the viruses. Anti-IBDV antibodies are quantitated with a commercial IBDV ELISA kit (ID SCREEN IBD VP2; IDVet). All chickens except Group 1 are challenged with $10^3$ mean embryo infectious dose ($EID_{50}$) of virulent IBDV standard challenge (STC) strain via oral route. Chickens are observed daily for clinical signs associated with IBD, such as depression and death. Seven days post challenge, chickens are necropsied and observed for grossly observable bursal lesions such as edema, discoloration, atrophy, hemorrhage, and yellow or gelatinous exudates. Weights of body and bursa are also measured at necropsy for calculation of B/B index, which is the ratio between the weight of the bursa and the body weight of challenged birds divided by the same ratio of non-challenged birds.

The results of this trial allow to confirm safety, stability, and effective expression in vivo.

LIST OF SEQUENCES

SEQ ID NO: 1 F-rpsL: (5'-GGCCTGGTGATGATGGCGGGATCGTTGTAT-3')

SEQ ID NO: 2 R-SV40promoter-neoR-rpsL: (5'-CCATGGTGCTGCGCTCAGAAGAACTCGTCA-3')

SEQ ID NO: 3 rpsLneo: (5'-
GGCCTGGTGATGATGGCGGGATCGTTGTATATTTCTTGACACCTTTTCGGCA
TCGCCCTAAAATTCGGCGTCCTCATATTGTGTGAGGACGTTTTATTACGTGT
TTACGAAGCAAAAGCTAAAACCAGGAGCTATTTAATGGCAACAGTTAACCA
GCTGGTACGCAAACCACGTGCTCGCAAAGTTGCGAAAAGCAACGTGCCTGC
GCTGGAAGCATGCCCGCAAAAACGTGGCGTATGTACTCGTGTATATACTAC
CACTCCTAAAAAACCGAACTCCGCGCTGCGTAAAGTATGCCGTGTTCGTCTG
ACTAACGGTTTCGAAGTGACTTCCTACATCGGTGGTGAAGGTCACAACCTGC
AGGAGCACTCCGTGATCCTGATCCGTGGCGGTCGTGTTAAAGACCTCCCGG
GTGTTCGTTACCACACCGTACGTGGTGCGCTTGACTGCTCCGGCGTTAAAGA
CCGTAAGCAGGCTCGTTCCAAGTATGGCGTGAAGCGTCCTAAGGCTTAAGG
AGGACAATCATGATTGAACAAGATGGATTGCACGCAGGTTCTCCGGCCGCT
TGGGTGGAGAGGCTATTCGGCTATGACTGGGCACAACAGACAATCGGCTGC
TCTGATGCCGCCGTGTTCCGGCTGTCAGCGCAGGGGCGCCCGGTTCTTTTTG
TCAAGACCGACCTGTCCGGTGCCCTGAATGAACTGCAGGACGAGGCAGCGC
GGCTATCGTGGCTGGCCACGACGGGCGTTCCTTGCGCAGCTGTGCTCGACGT
TGTCACTGAAGCGGGAAGGGACTGGCTGCTATTGGGCGAAGTGCCGGGGCA
GGATCTCCTGTCATCTCACCTTGCTCCTGCCGAGAAAGTATCCATCATGGCT

| LIST OF SEQUENCES |
|---|
| GATGCAATGCGGCGGCTGCATACGCTTGATCCGGCTACCTGCCCATTCGACC<br>ACCAAGCGAAACATCGCATCGAGCGAGCACGTACTCGGATGGAAGCCGGTC<br>TTGTCGATCAGGATGATCTGGACGAAGAGCATCAGGGGCTCGCGCCAGCCG<br>AACTGTTCGCCAGGCTCAAGGCGCGCATGCCCGACGGCGAGGATCTCGTCG<br>TGACCCATGGCGATGCCTGCTTGCCGAATATCATGGTGGAAAATGGCCGCTT<br>TTCTGGATTCATCGACTGTGGCCGGCTGGGTGTGGCGGACCGCTATCAGGAC<br>ATAGCGTTGGCTACCCGTGATATTGCTGAAGAGCTTGGCGGCGAATGGGCT<br>GACCGCTTCCTCGTGCTTTACGGTATCGCCGCTCCCGATTCGCAGCGCATCG<br>CCTTCTATCGCCTTCTTGACGAGTTCTTCTGA-3')<br><br>SEQ ID NO: 4 F-neoR-SV40promoter: (5'-<br>ACGAGTTCTTCTGAGCGCAGCACCATGGCC-3')<br><br>SEQ ID NO: 5 R-dsRed-SV40promoter-intron: (5'-<br>TCGGAGGAGGCCATCCTTAAGAGCTGTAAT-3')<br><br>SEQ ID NO: 6 F-SV40promoter-intron-dsRed: (5'-<br>TACAGCTCTTAAGGATGGCCTCCTCCGAGA-3')<br><br>SEQ ID NO: 7 R-SV40polyA-dsRed: (5'-<br>GCAGTGAAAAAAATGCTTTATTTGTGAAAT-3')<br><br>SEQ ID NO: 8 F-DEV-US4-rpsLneo: (5'-<br>ATGGCAACAATGATAGCTGTGGTGTTAGTTTTTTTGGGACGCGTTTTAGGGG<br>CCTGGTGATGATGGCGGG-3')<br><br>SEQ ID NO: 9 R-DEV-US4-rpsLneoSV40DsRed: (5'-<br>TTAAACTAATGGAACGCGTTGGAATTTCAAGTCTTGGCGCCCAAACATCGG<br>CAGTGAAAAAAATGCTTTA-3')<br><br>SEQ ID NO: 10 F-DEV-US5-rpsLneo: (5'-<br>ATGTATACAGACGTTACGGTCATGTGGGTAGCCGTGATTTTATTTACTATGG<br>CCTGGTGATGATGGCGGG-3')<br><br>SEQ ID NO: 11 R-DEV-US5-rpsLneoSV40DsRed: (5'-<br>TCATACCATACAAAGGCATAGGTACAGCCCACAGGTTAAAAACAAAGAAA<br>GCAGTGAAAAAAATGCTTTA-3')<br><br>SEQ ID NO: 12 F-VAC-136981: (5'-<br>AAGTGTATAAATTAGACAAGTAGCTATGCG-3')<br><br>SEQ ID NO: 13 R-neo: (5'-TCAGAAGAACTCGTCAAGAAGGC-3')<br><br>SEQ ID NO: 14 F-VAC-138520: (5'-GTTTATATTGACGCGGAATGTTGAC-3')<br><br>SEQ ID NO: 15 R-VAC-138560: (5'-CATTTTAACCGTTTAAGTCAACATTCCGC-3')<br><br>SEQ ID NO: 16 R-VAC-140339: (5'-ACTGAGATGTTGGACCATCAAATCCTG-3')<br><br>SEQ ID NO: 17 F-SphI-KAPEVAC-138500: (5'-gcGCATGCTAGCTGATCTAACTTTAC-3')<br><br>SEQ ID NO: 18 R-KAPE-US45del-SfiIinsertion: (5'-<br>GGTGGCCAATAAGGCCTGACGGCAATATGT-3')<br><br>SEQ ID NO: 19 F-KAPE-US45del-SfiIinsertion: (5'-<br>TCAggccttattggccACCAGCTACACAAG-3')<br><br>SEQ ID NO: 20 R-EcoRI-KAPEVAC-142750: (5'-gcGAATTCGATTAATTCTCCCGAACTGTTG-3')<br><br>SEQ ID NO: 21 chicken Beta-actin promoter: (5'-<br>tgcagctcagtgcatgcacgctcattgccatcgctatccctgcctctcctgctggcgctccccgggaggtgacttcaagggga<br>ccgcaggaccacctcggggggtgggggggagggctgcacacgcggaccccgctcccccctcccaacaaagcactgtggaat<br>caaaaaggggggaggggggatggaggggcgcgtcacaccccgccccacaccctcacctcgaggtgagcccacgttct<br>gcttcactctccccatctcccccccctcccaccccaatttttgtatttatttatttttttaattattttgtgcagcgatggggcggg<br>ggggggggcgcgcgccaggcggggcgggcgggccaggggcgggcgggcgaggcggagaggtgcggcg<br>gcagccaatcagagcggcgcgctccgaaagtttcctttatggcgaggcggcggcggcggcggccctataaaaagcgaag<br>cgcgcggcgggcgggagtcgctgcgcgctgccttcgccccgtgccccgctccgccgccgcctcgcgcgccgcccccgg<br>ctctgactgaccgcgttactcccacaggtgagcgggcgggacggccttctcctccgggctgtaattagcgcttggtttaatga<br>cggctcgtttcttttctgtggctgcgtgaaagccttaaagggctccgggagggccattgtgcgggggggagcggctcgggg<br>ggtgcgtgcgtgtgtgtgcgtggggagcgccgcgtgcggctccgcgctgcccggcggctgtgagcgctgcgggcgcg<br>gcgcggggattgtgcgctccgcagtgtgcgcgaggggagcgcggccggggcggtgccccgcggtgcgggggggct<br>gcgaggggaacaaaggctgcgtgcggggtgtgtgcgtggggggtgagcagggggtgtgggcgcggcggtcgggctgt<br>aaccccccctgcacccccctccccgaagttgctgagcacgaccccggcttcgggtgcggggctcctgtcggggcgtggcg<br>cggggctcgccgtgccgggcgggggtggcggcaggtgggggtgccggcgggcggggccgcctcgggccgggga<br>gggctcgggggaggggcgcggcggcccccggagcgccggcggctgtcgaggcgcggcgagccgcagccattgccttt<br>atggtaatcgtgcgagagggcgcagggacttcctttgtcccaaatctgtgcggagccgaaatctgggaggcgccgccgcac<br>ccctctagcgggcgcggggcgaagcggtgcggcgccggcaggaaggaaatgggcggggagggccttcgtgcgtcgcc |

LIST OF SEQUENCES gcgccgccgtcccttctccatctccagcctcggggctgtccgcaggggacggctgccttcggggggacgggcaggg
cggggttcggcttctggcgtgtgaccggcggggtttatatcttcccttctctgttcctccgcagccccc-3')

SEQ ID NO: 22 F-KAPEVAC-138407: (5'-GTCCACTATGCCATGACATAGGTG-3')

SEQ ID NO: 23 STC1109S: (5'-GAGCAACTTCGAGCTGATCC-3')

SEQ ID NO: 24 STC201AS: (5'-GCCAGGGAATCCAGGGAAAAAGAC-3')

SEQ ID NO: 25 Coa5 promoter:
(5'-TATTTTGTGCAGCGATGGGGCGGGGGGGGGGGGGCGCGCGCCAGGC
GGGGCGGGGCGGGGCGAGGGGCGGGGCGGGGCGAGGCGGAGAGGTGCGG
CGGCAGCCAATCAGAGCGGCGCGCTCCGAAAGTTTCCTTTTATGGCGAGGC
GGCGGCGGCGGCGGCCCTATAAAAAGCGAAGCGCGCGGCGGGCGGGAGT
CGCTGCGCGCTGCCTTCGCCCCGTGCCCCGCTCCGCCGCCGCCTCGCGCCG
CCCGCCCCGGCTCTGACTGACCGCGT-3')

SEQ ID NO: 26 R-KAPE-US45del: (5'-GCTTGTGTAGCTGGTTGACGGCAATATG-3')

SEQ ID NO: 27 F-KAPE-US45del: (5'-CATATTGCCGTCAACCAGCTACACAAGC-3')

SEQ ID NO: 28 F-SphI-KAPEVAC-76350: (5'-GCGCATGCCAATTGTCTAATTCCAG-3')

SEQ ID NO: 29 R-KAPE-UL23del-SfiIinsertion: (5'-CCCGGCCAATAAGGCCACAGAAAAAGCGCG-3')

SEQ ID NO: 30 F-KAPE-UL23del-SfiIinsertion: (5'-CTGTGGCCTTATTGGCCGGGATCTGGAAC-3')

SEQ ID NO: 31 R-EcoRI-KAPEVAC-78350: (5'-GCGAATTCATGTGCTACGCCCAG-3')

SEQ ID NO: 32 F-SalI-VAC68400: (5'-CGGTCGACACTCCCAGGGGTGAAGC-3')

SEQ ID NO: 33 R-SfiI-UL26-27-insertion: (5'-CGGCCAATAAGGCCAAGAATGCATTCGGCC-3')

SEQ ID NO: 34 F-SfiI-UL26-27-insertion: (5'-TGGCCTTATTGGCCGCCGTATGAATTGCGC-3')

SEQ ID NO: 35 R-SacI-VAC69400: (5'-GCGAGCTCCTGCAACCACAGACCGC-3')

SEQ ID NO: 36 F-SalI-VAC21300: (5'-CGGTCGACATAGAACGCGCTTCATCTAA-3')

SEQ ID NO: 37 R-SfiI-UL45-46-insertion: (5'-TGGCCAATAAGGCCGTTTATTGTTTATTAT-3')

SEQ ID NO: 38 F-SfiI-UL45-46-insertion: (5'-CGGCCTTATTGGCCAATCTGATTCATCCAA-3')

SEQ ID NO: 39 R-SacI-VAC22300: (5'-GCGAGCTCCGCCTAATCACAATCGGTATTG-3')

SEQ ID NO: 40 F-SphI-VAC12000: (5'-CCGCATGCGCAACTATATATGTCGGTC-3')

SEQ ID NO: 41 R-SfiI-UL50-51-insertion: (5'-GGGCCAATAAGGCCCAAAAGTACATTTTGT-3')

SEQ ID NO: 42 F-SfiI-UL50-51-insertion: (5'-GGGCCTTATTGGCCCAATTTATTTACTATT-3')

SEQ ID NO: 43 R-EcoRI-VAC13000: (5'-GCGAATTCTGGATATGATATACCGTTGC-3')

The invention claimed is:

1. A Duck Enteritis Virus (DEV), wherein said virus has inactive US4 and US5 genes.

2. The DEV of claim 1, wherein said US4 and US5 genes are, independently from each other, mutated, deleted, or interrupted.

3. The DEV of claim 2, wherein at least 20% of the coding sequence of each of said US4 and US5 genes is deleted.

4. The DEV of claim 1, wherein the intergenic region between US4 and US5 genes is deleted.

5. The DEV of claim 2, wherein said virus comprises a deletion of a nucleotide region comprising at least 50% of the US4 gene, all of the intergenic region between the US4 gene and the US5 gene, and at least 50% of the US5 gene.

6. The DEV of claim 1, wherein said virus further comprises an inactive UL23, US7 and/or UL4 gene.

7. The DEV of claim 6, wherein said virus comprises (i) a deletion of a nucleotide region comprising at least 50% of the US4 gene, all of the intergenic region between the US4 gene and the US5 gene, and at least 50% of the US5 gene and (ii) a deletion of at least 50% of the UL23 gene sequence.

8. The DEV of claim 6, wherein said virus comprises (i) a deletion of a nucleotide region comprising at least 50% of the US4 gene, all of the intergenic region between the US4 gene and the US5 gene, and at least 50% of the US5 gene and (ii) a deletion of at least 50% of the US7 gene sequence.

9. The DEV of claim 6, wherein said virus comprises (i) a deletion of a nucleotide region comprising at least 50% of the US4 gene, all of the intergenic region between the US4 gene and the US5 gene, and at least 50% of the US5 gene and (ii) a deletion of at least 50% of the UL4 gene sequence.

10. The DEV of claim 1, which further comprises a foreign nucleic acid.

11. The DEV of claim 10, wherein the foreign nucleic acid is located in the inactive US4 or US5 gene.

12. The DEV of claim 11, wherein said virus comprises a deletion of a nucleotide region comprising at least 50% of the US4 gene, all of the intergenic region between the US4 gene and the US5 gene, and at least 50% of the US5 gene, and wherein the foreign nucleic acid is located in place of said deleted region.

13. The DEV of claim 10, wherein the foreign nucleic acid is located in an insertion site selected from the UL4 gene, the UL44 gene, the UL27-UL26 intergenic region, the UL23 gene, the UL45-UL46 intergenic region, the UL50-UL51 intergenic region, the US7 gene, the US7-US8 intergenic region, or the US10 gene.

14. The DEV of claim 10, wherein the foreign nucleic acid encodes an antigen or an immunostimulatory molecule, or an avian pathogen antigen.

15. The DEV of claim 14, wherein the antigen is an antigenic protein or peptide of avian paramyxovirus type 1, an antigenic peptide of Gumboro disease virus, an antigenic peptide of the infectious laryngotracheitis virus (ILTV), an antigenic peptide of *Mycoplasma gallisepticum* and an antigenic peptide of an avian influenza virus.

16. The DEV of claim 15, wherein the antigenic peptide is a VP2 protein of IBDV or an immunogenic fragment thereof, or a hemagglutinin (HA) protein of an influenza virus or an immunogenic fragment thereof.

17. The DEV of claim 14, wherein the antigen is selected from F protein of a Newcastle disease virus (NDV) or a fragment thereof, VP2 protein of an Infectious bursal disease virus (IBDV) or a fragment thereof, gB protein or a fragment thereof of an infectious laryngotracheitis virus (ILTV), a 40K protein of *Mycoplasma gallisepticum* or a fragment thereof, and a surface protein hemagglutinin (HA) of an avian influenza virus or a fragment thereof.

18. A nucleic acid molecule comprising the genome of a DEV of claim 1.

19. A host cell comprising a DEV of claim 1 or a nucleic acid molecule comprising the genome of said DEV.

20. A method for producing or replicating a DEV, comprising infecting a competent cell with a DEV of claim 1 or a nucleic acid molecule comprising the genome of said DEV, and collecting the DEV produced by the competent cell.

21. A method of vaccinating or immunizing poultry comprising administering the DEV of claim 1 or a nucleic acid molecule comprising the genome of said DEV to poultry.

22. The method of claim 21, wherein the DEV is administered by injection.

23. The method of claim 21, wherein the DEV is administered in ovo or at day1 or day2 post-hatch.

24. A method of inducing protective immunity in poultry comprising administering the DEV of claim 1 or a nucleic acid molecule comprising the genome of said DEV to poultry.

25. A composition comprising a DEV of claim 1 or a nucleic acid molecule or host cell comprising the genome of said DEV and a pharmaceutically or veterinary acceptable excipient or carrier.

26. The composition of claim 25, which further comprises an adjuvant.

27. A vaccination kit for immunizing an avian, which comprises the following components:
   a) an effective amount of a composition of claim 1; and
   b) a means for administering said composition to said avian.

28. The DEV of claim 1, said DEV comprising inactivated US4 and US5 genes, the US4 gene corresponding to nucleotides 141123 to nucleotides 142502 of a CSC strain genome or nucleotides corresponding to the US4 gene in another DEV strain, and the US5 gene corresponding to nucleotides 142662 to nucleotides 144281 of a CSC strain genome or nucleotides corresponding to the US5 gene positions in another DEV strain.

* * * * *

UNITED STATES PATENT AND TRADEMARK OFFICE
CERTIFICATE OF CORRECTION

PATENT NO.         : 10,821,170 B2
APPLICATION NO.    : 16/313174
DATED              : November 3, 2020
INVENTOR(S)        : Saeki Yukari and Shuji Saitoh It is certified that error appears in the above-identified patent and that said Letters Patent is hereby corrected as shown below:

In the Specification

Column 13,
Line 31, "VP2, FIN" should read --VP2, HN--.

Signed and Sealed this
Fifth Day of October, 2021

Drew Hirshfeld
*Performing the Functions and Duties of the*
*Under Secretary of Commerce for Intellectual Property and*
*Director of the United States Patent and Trademark Office*